(12) United States Patent
Hausheer

(10) Patent No.: US 8,143,236 B2
(45) Date of Patent: *Mar. 27, 2012

(54) CHEMOPROTECTIVE METHODS

(75) Inventor: Frederick H. Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 666 days.

This patent is subject to a terminal disclaimer.

(21) Appl. No.: 12/075,898

(22) Filed: Mar. 14, 2008

(65) Prior Publication Data

US 2008/0193498 A1  Aug. 14, 2008

Related U.S. Application Data

(63) Continuation-in-part of application No. 11/638,193, filed on Dec. 13, 2006, now Pat. No. 8,026,227.

(51) Int. Cl.
*A61K 31/665* (2006.01)
*A61K 31/66* (2006.01)
*A61K 31/28* (2006.01)

(52) U.S. Cl. ........ 514/100; 514/102; 514/108; 514/126; 514/492

(58) Field of Classification Search ............... 514/2, 4, 514/12, 21, 23, 102, 126, 178, 182, 238, 514/263.31, 266.1, 285, 413, 449, 459, 460, 514/492, 517, 589, 649, 672, 772
See application file for complete search history.

(56) References Cited

U.S. PATENT DOCUMENTS

| | | | | |
|---|---|---|---|---|
| 5,919,816 A | * | 7/1999 | Hausheer et al. | 514/449 |
| 6,040,294 A | * | 3/2000 | Hausheer et al. | 514/23 |
| 6,040,304 A | * | 3/2000 | Hausheer et al. | 514/221 |
| 6,040,312 A | * | 3/2000 | Hausheer et al. | 514/283 |
| 6,043,249 A | * | 3/2000 | Hausheer et al. | 514/266.1 |
| 6,046,159 A | * | 4/2000 | Hausheer et al. | 514/2 |
| 6,046,234 A | * | 4/2000 | Hausheer et al. | 514/517 |
| 6,048,849 A | * | 4/2000 | Hausheer et al. | 514/178 |
| 6,057,361 A | * | 5/2000 | Hausheer et al. | 514/460 |
| 6,066,645 A | * | 5/2000 | Hausheer et al. | 514/283 |
| 6,066,668 A | * | 5/2000 | Hausheer et al. | 514/492 |
| 6,100,247 A | * | 8/2000 | Hausheer et al. | 514/108 |

OTHER PUBLICATIONS van den Bent, "Prevention of Chemotherapy-Induced Neuropathy: Leukemia Inhibitory Factor", Clinical Cancer Research, vol. 11, No. 5, pp. 1691-1693 (Mar. 1, 2005).*

* cited by examiner

*Primary Examiner* — Kevin E Weddington
(74) *Attorney, Agent, or Firm* — Scott A. Whitaker

(57) ABSTRACT

Compositions and methods for reducing, preventing, mitigating, and/or delaying the onset of, attenuating the severity of, and/or hastening the resolution of, for example, one or more chemotherapy-associated toxicities in a subject receiving one or more chemotherapeutic agents. In addition compositions and methods for mitigating or preventing a novel form of chemotherapy-induced peripheral neuropathy are disclosed and claimed.

14 Claims, 5 Drawing Sheets

Fig. 1

|  | 30 min Infusion (N=257) | 30 & 45 min Infusions (N=148) | 45 min Infusion (N=50) |
|---|---|---|---|
| Number of Patients with at Least One Hypersensitivity Adverse Event | 108 (42.0%) | 40 (27.0%) | 15 (30.0%) |
| Total Number of Hypersensitivity Adverse Event | 314 | 137 | 29 |
| Mean Time to First Hypersensitivity Event | 23.9 | 69.6 | 91.6 |
|  |  |  |  |
| IMMUNE SYSTEM DISORDERS | 32 (12.5%) | 9 (6.1%) | 6 (12.0%) |
| ANAPHYLACTIC SHOCK | 0 (0.0%) | 0 (0.0%) | 1 (2.0%) |
| DRUG HYPERSENSITIVITY | 4 (1.6%) | 0 (0.0%) | 3 (6.0%) |
| HYPERSENSITIVITY | 28 (10.9%) | 9 (6.1%) | 2 (4.0%) |
|  |  |  |  |
| RESPIRATORY, THORACIC AND MEDIASTINAL DISORDERS | 39 (15.2%) | 6 (4.1%) | 2 (4.0%) |
| APNOEA | 2 (0.8%) | 0 (0.0%) | 0 (0.0%) |
| DYSPNOEA | 36 (14.0%) | 6 (4.1%) | 2 (4.0%) |
| DYSPONOEA EXACERBATED | 1 (0.4%) | 0 (0.0%) | 0 (0.0%) |
|  |  |  |  |
| SKIN AND SUBCUTANEOUS TISSUE DISORDERS | 51 (19.8%) | 19 (12.8%) | 7 (14.0%) |
| DERMATITIS ALLERGIC | 8 (3.1%) | 11 (7.4%) | 2 (4.0%) |
| ERYTHEMA | 17 (6.6%) | 3 (2.0%) | 2 (4.0%) |
| RASH | 27 (10.5%) | 3 (2.0%) | 1 (2.0%) |
| RASH ERYTHEMATOUS | 1 (0.4%) | 0 (0.0%) | 0 (0.0%) |
| RASH GENERALISED | 1 (0.4%) | 1 (0.7%) | 0 (0.0%) |
| RASH MACULAR | 1 (0.4%) | 0 (0.0%) | 0 (0.0%) |
| URTICARIA | 5 (1.9%) | 1 (0.7%) | 2 (4.0%) |
|  |  |  |  |
| VASCULAR DISORDERS | 35 (13.6%) | 14 (9.5%) | 2 (4.0%) |
| FLUSHING | 18 (7.0%) | 13 (8.8%) | 1 (2.0%) |
| HOT FLUSH | 9 (3.5%) | 0 (0.0%) | 1 (2.0%) |
| HYPOTENSION | 16 (6.2%) | 1 (0.7%) | 0 (0.0%) |

Fig. 2

| Administration Parameter and Drug Concentration | 30 minutes (n = 171) 200 mg/mL | 30 & 45 minutes (n = 109) 200 mg/mL @ 30 minutes 100 mg/mL @ 45 minutes | 45 minutes (n = 93) 100 mg/mL |
|---|---|---|---|
| Patients experiencing at least one drug-related SAE | 13 (7.6%) | 4 (3.7%) | 5 (5.4%) |
| Patients experiencing at least one drug-related grade 3 AE | 28 (16.4%) | 7 (6.4%) | 8 (8.6%) |

Fig. 3

Primary Endpoint - PNQ (GEE Method)

Test of Each Factor

| Factor | Degree of freedom | Chi-square statistics | P - value |
|---|---|---|---|
| Drug | 1 | 2.0080 | 0.1565 |
| Cycle | 5 | 63.2192 | <0.0001 |
| Age | 3 | 3.6337 | 0.3038 |
| Drug×Cycle | 5 | 5.4706 | 0.3612 |
| Drug×Age | 3 | 0.1735 | 0.6771 |

Fig. 4

| Secondary Endpoint – PNQ, NCI - CTC | | |
|---|---|---|
| | PNQ | NCI-CTC |
| GEE | 0.1778 | 0.3038 |
| Mantel Test | 0.7939 | 0.6526 |

Fig. 5

| Item | Group | Peripheral Neuropathy – Mantel Test | | | | | | Degree of freedom | Chi-square statistics | Mantel P value |
| --- | --- | --- | --- | --- | --- | --- | --- | --- | --- | --- |
| | | A | B | C | D | E | Total | | | |
| PNQ Q1 & Q2 | BNP7787 | 8 | 45 | 31 | 6 | 1 | 91 | 1 | 0.0296 | 0.8635 |
| | Placebo | 12 | 42 | 23 | 13 | 1 | 91 | | | |

CHEMOPROTECTIVE METHODS

RELATED APPLICATIONS

The present application is a Continuation-in-Part of, and claims priority to Published patent application Ser. No. 11/638,193, with a filing date of Dec. 13, 2006 now U.S. Pat. No. 8,026,227, and entitled: "CHEMOPROTECTIVE METHODS AND COMPOSITIONS".

FIELD OF THE INVENTION

The field comprises pharmaceuticals and pharmaceutical treatments, including, for example, (i) methods of administering chemoprotective compounds and chemotherapeutic agents; (ii) formulations comprising chemoprotective compounds and/or chemotherapeutic agents; (iii) delivery devices containing compounds and/or formulations; and (iv) methods of using formulations and devices to treat subjects in need thereof. In addition compositions and methods for mitigating or preventing a novel form of chemotherapy-induced peripheral neuropathy are disclosed and claimed.

BACKGROUND OF THE INVENTION

Anti-cancer therapy, such as the administration of chemotherapeutic agents, is associated with Adverse Events including chemotherapy-associated toxicities. Chemotherapy-associated toxicities include, for example, neurotoxicity, nephrotoxicity, ototoxicity, allergic or hypersensitivity reactions, hepatic toxicity, myelosuppression, as well as other toxicities.

Chemotherapy-associated toxicities can materially offset or limit the potential benefits to the patient undergoing treatment. By way of non-limiting example, chemotherapy-associated toxicity can result in treatment delays, treatment interruptions, dose modifications, dose schedule modifications, or even complete cessation of treatment. Thus, in addition to their adverse pharmacological affects, the development of chemotherapy-associated toxicities can limit or curtail the effectiveness of the primary treatment of the patient's cancer or preclude it all together. Cessation, interruption, or delays in patient treatment, or reducing the dosage of chemotherapeutic therapy, for example, may be detrimental to a subject's chances of long-term survival or control of the cancer, since the interruption, delay, reduction in dose, or cessation of chemotherapy can allow the progression of cancer within the subject. In some instances, it is well recognized that these chemotherapy-associated toxicities can be so severe and/or protracted that they are immediately life-threatening or fatal to the patient.

Currently, there are approximately twenty recognized classes of FDA-approved chemotherapeutic agents. These classifications are generalizations based upon either a common structure shared by the particular agents (i.e., structure-based classes) or upon a common identified mechanism(s) of action of the particular agents (i.e., mechanism-based classes); in many instances these classifications identify the same compounds by different classification approaches. Structural-based classes of chemotherapeutic agents include, for example: fluoropyrimidines; pyrimidine nucleosides; purines; anti-folates, platinum analogs; electrophilic alkylating agents; anthracyclines/anthracenediones; podophyllotoxins; camptothecins; hormones and hormonal analogs; enzymes, proteins, and antibodies, vinca alkaloids, taxanes and epothilones.

Mechanism-based classes of chemotherapeutic agents include, for example: antihormonals; antimirotubule agents, alkylating agents (classical and non-classical), antimetabolites, topoisomerase inhibitors, antivirals, and miscellaneous cytotoxic and cytostatic agents.

Taxane chemotherapeutic agents have been used to treat subjects with breast, ovarian, lung, bladder, and esophageal cancer, among others. Representatives of taxanes include paclitaxel, including without limitation, e.g., taxol, abraxane, and the like, and analogs thereof, including, without limitation, polyglutamylated forms of paclitaxel (Xyotax™), liposomal paclitaxel (Tocosol™), and docetaxel and analogs and formulations thereof. However, the administration of taxanes, for example, is commonly limited due to the development of serious and potentially life-threatening toxicities. In particular, the clinical use of taxanes frequently involves delay, modification, or discontinuance of use due to chemotherapy-associated toxicities including toxic disorders of peripheral nerve systems (including chemotherapy-induced peripheral neuropathy) resulting in numbness, burning, pain, paresthesias, dysesthesias, sensory loss, weakness, paralysis, arthralgia, myalgia, as well as other toxicities and Adverse Events (including, for example, hepatotoxicity and myelosuppression).

Platinum analog chemotherapeutic agents have been used to treat subjects with lung, head, neck, ovary, esophagus, bladder, testis, and other cancers. By way of non-limiting example, the valence of the platinum ligand contained therein may be platinum II or platinum IV. The platinum medicaments or platinum compounds of the present invention include, in a non-limiting manner, cisplatin, oxaliplatin, carboplatin, satraplatin, and derivatives thereof. Like the taxanes and other chemotherapeutic drugs, platinum analogs are associated with a number of toxicities, including nephrotoxicity, bone marrow suppression, neurotoxicity, nausea, vomiting, and others.

Amifostine (Ethyol®) and 2-mercapto ethane sulfonate sodium are FDA-approved cytoprotective agents for use in preventing and mitigating chemotherapy agent-associated Adverse Events. Amifostine is currently approved to help prevent cisplatin-induced nephrotoxicity. Problematically, however, amifostine administration has been observed to result in increased intrinsic adverse effects, such as nausea, vomiting, and severe hypotension and has not been shown to reduce or prevent neurotoxicity. 2-mercapto ethane sulfonate sodium, also known as mesna, is used to help prevent hemorrhagic toxicity to the uroepithelial tract (e.g., primarily ureters, urethra and bladder) associated with the administration of oxazaphosphorine chemotherapy, particularly ifosphamide and, less commonly, cyclophosphamide. Mesna administration, even to healthy volunteers, has been observed to result in various adverse chemotherapy-associated Adverse Events including, for example, nausea, vomiting, hypotension, pain, and diarrhea. See, e.g. *Physicians Desk Reference* (PDR) and *American Hospital Formulary Service* (AHFS).

There remains an unmet need for chemoprotective agents and compositions and methods of their administration that are optimally capable of reducing, preventing, mitigating, and/or delaying chemotherapy-associated toxicities, and which also do not result in either the addition of, or the augmentation of medically-unacceptable adverse effects that may otherwise limit or interfere with the safety and utility of the chemoprotectant agent in the subjects.

Ideal properties of a chemoprotective agent, composition, and/or regime include: (i) maximum reduction, prevention, mitigation, and/or delay in onset of chemotherapy-associated toxicities (and associated treatment interruptions, delays or dose modifications due to such toxicities); (ii) a lack of interference with anti-tumor activity and lack of tumor desensitization to cytotoxic effects of chemotherapy; (iii) a safety profile that is medically acceptable; (iv) exploitation of biochemical and pharmacological mechanisms to reduce, prevent, mitigate, and/or delay chemotherapy-associated toxicity; and (v) increases in chemotherapeutic index by allowing increases in dose, frequency, and/or duration of primary chemotherapy treatment. If a chemoprotective agent is capable of increasing the therapeutic index of an active, but otherwise toxic, chemotherapy drug, composition, and/or regimen it may lead to significant benefit to the subject by increasing tumor response rate, increasing time to tumor progression, and overall patient survival.

The inventor has previously disclosed the use of, for example, 2,2'-dithio-bis ethane sulfonate and other dithioethers: (i) to prevent and decrease nephrotoxicity (see, for example, U.S. Pat. Nos. 5,789,000; 5,866,169; 5,866,615; 5,866,617; 5,902,610) and (ii) to increase the therapeutic index of antineoplastic agents (see, for example, U.S. Pat. No. 6,037,336). Disodium 2,2'-dithio-bis ethane sulfonate has been referred to as dimesna, Tavocept®, and BNP7787 in the literature.

The present invention provides methods, as well as compositions and formulations and methods for their administration, to achieve higher degrees of patient safety and patient benefit while maintaining or increasing the therapeutic index and preventing and reducing chemotherapy-associated toxicities, including those toxicities described in the above-noted patents and patent applications. By significantly increasing the degree of safety of the patient's overall treatment with chemotherapy and reducing adverse physiological responses to chemotherapeutic pharmacological intervention, the methods, compositions and formulations of this invention will, for example: (i) allow physicians to administer increased dose levels of chemotherapeutic agents, (ii) allow administration of chemotherapeutic agents more frequently, i.e., with shorter time intervals between treatment or actual treatment time; (iii) allow increases in the number of chemotherapy treatments by the prevention of cumulative toxicities; (iv) any combination of numbers (i)-(iii) above, and/or (v) allow reduced numbers of instances of dose modifications, treatment interruptions or delays, or discontinued treatments, alone or in combination with beneficial patient outcomes, as described in numbers (i)-(iv) above.

SUMMARY OF THE INVENTION

The invention described and claimed herein has many attributes and embodiments including, but not limited to, those set forth or described or referenced in this Summary. This Summary is not intended to be all-inclusive and the invention described and claimed herein is not limited to or by the features or embodiments identified in this Summary, which is included for purposes of illustration only and not restriction.

The invention includes methods, formulations and devices, and uses of the foregoing.

The methods, formulations and devices may be used for reducing, preventing, mitigating, delaying the onset of, attenuating the severity of, and/or hastening the resolution of toxicity in a subject receiving a chemotherapeutic agent.

Methods include administering to a subject who is receiving or will receive a chemotherapeutic agent, an effective amount of a 2,2'-dithio-bis-ethane sulfonate, a pharmaceutically-acceptable salt thereof, and/or an analog thereof, which include the compounds of Formula (I), administered at a rate of about 0.1 g/min. to about 2.0 g/min. to the subject In another embodiment, an effective amount of a 2,2'-dithio-bis-ethane sulfonate, a pharmaceutically-acceptable salt thereof, and/or an analog thereof, which include the compounds of Formula (I), is administered at a rate of about 0.2 g/min. to about 1.0 g/min. to the subject.

In another embodiment, an effective amount of a 2,2'-dithio-bis-ethane sulfonate, a pharmaceutically-acceptable salt thereof, and/or an analog thereof, which include the compounds of Formula (I), is administered at a rate of about 0.7 g/min. to the subject.

In one embodiment, a dose of a 2,2'-dithio-bis-ethane sulfonate, a pharmaceutically-acceptable salt thereof, and/or an analog thereof, which include the compounds of Formula (I), is administered over a period of about 45 minutes to the subject.

In another embodiment, the total dose of a 2,2'-dithio-bis-ethane sulfonate, a pharmaceutically-acceptable salt thereof, and/or an analog thereof, which include the compounds of Formula (I), administered to a subject is from about 4.0 g/m$^2$ to about 35 g/m$^2$. One preferred dose is about 18.4 g/m$^2$. Particularly preferred is the administration of one or more of said doses of said compounds to a subject over about 45 minutes.

The invention also includes methods of reducing, preventing, mitigating, delaying the onset of, attenuating the severity of, and/or hastening the resolution of chemotherapy-associated toxicity in a subject receiving a chemotherapy agent, comprising administering to the subject an effective amount of a 2,2'-dithio-bis-ethane sulfonate, a pharmaceutically-acceptable salt thereof, and/or an analog thereof, which include the compounds of Formula (I), at a rate of about 0.1 g/min. to about 4.6 g/min., at a total dose of about 4 g/m$^2$ to about 35 g/m$^2$. Preferred is administration of a total dose of about 18.4 g/m$^2$ at a rate of about 0.1 g/min. to about 4.6 g/min. to a subject. Particularly preferred is administration of a total dose of about 18.4 g/m$^2$ over about 45 minutes to a subject at an administration rate of about 0.4 g/m$^2$/min.

In another embodiment, an effective amount of a 2,2'-dithio-bis-ethane sulfonate, a pharmaceutically-acceptable salt thereof, and/or an analog thereof, which include the compounds of Formula (I), is administered to a subject at a rate of about 1 mg/mL/min. to about 50 mg/mL/min.

In another embodiment of the invention, an effective amount of a 2,2'-dithio-bis-ethane sulfonate, a pharmaceutically-acceptable salt thereof, and/or an analog thereof, which include the compounds of Formula (I), is administered to a subject at a rate of about 7 mg/mL/min. In one embodiment a 2,2'-dithio-bis-ethane sulfonate, a pharmaceutically-acceptable salt thereof, and/or an analog thereof, which include the compounds of Formula (I), is administered to a subject over a period of about 45 minutes. In another embodiment a 2,2'-dithio-bis-ethane sulfonate, a pharmaceutically-acceptable salt thereof, and/or an analog thereof, which include the compounds of Formula (I), is administered to a subject in a formulation having a concentration of about 100 mg/mL of the chemoprotective agent. In yet another embodiment a 2,2'-dithio-bis-ethane sulfonate, a pharmaceutically-acceptable salt thereof, and/or an analog thereof, which include the compounds of Formula (I), is administered to a subject over a period of about 45 minutes and in a formulation having a concentration of about 100 mg/mL of the chemoprotective agent.

In another aspect of the invention, an effective amount of a 2,2'-dithio-bis-ethane sulfonate, a pharmaceutically-acceptable salt thereof, and/or an analog thereof, which include the compounds of Formula (I), is administered to a subject at a rate of about 7 mg/mL/min., for a period of about 45 minutes. In another aspect of the invention, an effective amount of a 2,2'-dithio-bis-ethane sulfonate, a pharmaceutically-acceptable salt thereof, and/or an analog thereof, which include the compounds of Formula (I), is administered to a subject at a rate of about 7 mg/mL/min., in a formulation having a concentration of about 100 mg/mL of the chemoprotective agent. In yet another aspect of the invention, an effective amount of a 2,2'-dithio-bis-ethane sulfonate, a pharmaceutically-acceptable salt thereof, and/or an analog thereof, which include the compounds of Formula (I), is administered to a subject at a rate of about 7 mg/mL/min., for a period of about 45 minutes, in a formulation having a concentration of about 100 mg/mL of the chemoprotective agent.

The invention also encompasses methods of reducing, preventing, mitigating, delaying the onset of, attenuating the severity of, and/or hastening the resolution of toxicity in a subject receiving a chemotherapeutic agent comprising administering to the subject, a composition comprising an effective amount of a 2,2'-dithio-bis-ethane sulfonate, a pharmaceutically-acceptable salt thereof, and/or an analog thereof, which include the compounds of Formula (I), wherein the composition has an osmolarity that is about 0.1- to about 5-times the osmolarity of the normal range of plasma osmolarity. Osmolarity is a measure of the osmoles (Osm) of solute per kilogram of solvent. In another aspect of the invention, the composition has an osmolarity that is about 2- to about 4-times the normal range of plasma osmolarity. In yet another aspect of the invention, the composition has an osmolarity that is about 3-times the normal range of plasma osmolarity, wherein the normal range of human plasma ranges from approximately 280 mOsm to approximately 320 mOsm.

Any one of the variables of dose, rate of administration, concentration of chemoprotective agent, formulation osmolarity, and infusion time may be combined with any one or more other of these variables, in the amounts and/or ranges set forth, to create a composition or formulation or method of administration for one or more of the described chemoprotective agents. For example, varying formulation osmolarity may be administered to the subject, as compared to the normal range of human plasma osmolarity (which ranges from approximately 280 mOsm to approximately 320 mOsm). Osmolarity is a measure of the osmoles of solute per kilogram of solvent.

In another embodiment, the 2,2'-dithio-bis-ethane sulfonate is a disodium salt.

In another embodiment, a 2,2'-dithio-bis-ethane sulfonate analog, including, for example, a compound of Formula (I), is a disodium salt.

In other embodiments, compounds of Formula (I) include, for example, monosodium 2,2'-dithio-bis-ethane sulfonate, sodium potassium 2,2'-dithio-bis-ethane sulfonate, dipotassium 2,2'-dithio-bis-ethane sulfonate, calcium 2,2'-dithio-bis-ethane sulfonate, magnesium 2,2'-dithio-bis-ethane sulfonate, monopotassium 2,2'-dithio-bis-ethane sulfonate, or manganese 2,2'-dithio-bis-ethane sulfonate; ammonium 2,2'-dithio-bis-ethane sulfonate. Mono- and di-potassium salts of 2,2'-dithio-bis-ethane sulfonate and/or an analog thereof, are generally administered to a subject if the total dose of potassium administered at any given point in time is not greater than 100 Meq. and the subject is not hyperkalemic and does not have a condition that would predispose the subject to hyperkalemia (e.g., renal failure).

In another embodiment, the 2,2'-dithio-bis-ethane sulfonate, a pharmaceutically-acceptable salt thereof, and/or an analog thereof, which include the compounds of Formula (I), is administered intravenously using the rates and/or times described herein, with or without using the concentrations and/or osmolarity ranges described herein, alone or in conjunction with a dose as described herein.

In another embodiment, the 2,2'-dithio-bis-ethane sulfonate, a pharmaceutically-acceptable salt thereof, and/or an analog thereof, which include the compounds of Formula (I), is administered from about once a day to about once every five weeks, including about once a week or less, about once every two weeks or less, about one every three weeks or less, about once every four weeks or less, about once every five weeks or less, and any daily or weekly interval in between.

In one embodiment, the 2,2'-dithio-bis-ethane sulfonate, a pharmaceutically-acceptable salt thereof, and/or an analog thereof, which include the compounds of Formula (I), is utilized to reduce, prevent, mitigate, delay the onset of, or attenuate one or more toxicities consequent to administration of a chemotherapeutic agent. Such toxicities may include, for example, neurotoxicity and nephrotoxicity. Reducing includes reducing, preventing, mitigating, delaying the onset of, attenuating the severity of, and/or hastening the resolution rate of at least one toxicity, typically an observed toxicity, consequent to administration of a chemotherapeutic agent.

In one embodiment, the 2,2'-dithio-bis-ethane sulfonate, a pharmaceutically-acceptable salt thereof, and/or an analog thereof, which include the compounds of Formula (I), is used to shorten the duration between treatment cycles of a chemotherapeutic agent.

In another embodiment, the 2,2'-dithio-bis-ethane sulfonate, a pharmaceutically-acceptable salt thereof, and/or an analog thereof, which include the compounds of Formula (I), is utilized to increase the dosage of a chemotherapeutic agent, preferably to a maximum useful amount.

In another embodiment, the 2,2'-dithio-bis-ethane sulfonate, a pharmaceutically-acceptable salt thereof, and/or an analog thereof, which include the compounds of Formula (I), is administered to shorten the duration between treatment cycles of a chemotherapeutic agent and allow a safe increase in the dosage or dosage rate (e.g., mg/day or week or mg/min.) of a chemotherapeutic agent administered.

In one embodiment, the 2,2'-dithio-bis-ethane sulfonate, a pharmaceutically-acceptable salt thereof, and/or an analog thereof, which include the compounds of Formula (I), is administered with a chemotherapeutic agent, either alone or in multiple chemotherapeutic agent combinations, without limitation, in accordance with medical indications involving the proper treatment of a subject's cancer.

In certain embodiments, the chemotherapeutic agent is, for example: a fluoropyrimidine; a pyrimidine nucleoside; a purine nucleoside; an antifolate, a platinum analog; an anthracycline/anthracenedione; an epipodophyllotoxin; a camptothecin; a hormone, a hormonal analog; an antihormonal; an enzyme, protein, peptide, or polyclonal and monoclonal antibody; a vinca alkaloid; a taxane; an epothilone; an antimicrotubule agent; an alkylating agent; an antimetabolite; a topoisomerase inhibitor; an antiviral; or another cytotoxic and/or cytostatic agent. Fluoropyrimidines include, for example, 5-fluorouracil (5-FU), S-1 capecitabine, ftorafur, 5'deoxyfluorouridine, UFT, eniluracil, and the like. Pyrimidine nucleosides include, for example, cytarabine, deoxycytidine, 5-azacytosine, gemcitabine, 5-azacytosine, 5-azadeoxycytidine, and the like. Purine nucleosides include, for example, fludarabine, 6-mercaptopurine, thioguanine, allopurinol, cladribine, and 2-chloro adenosine. Antifolates include, for example, methotrexate (MTX), trimetrexate, aminopterin, and methylene-10-deazaminopterin (MDAM). Platinum analogs include, for example, cisplatin, carboplatin, oxaliplatin, satraplatin, picoplatin, tetraplatin, platinum-DACH and analogs thereof. Anthracyclines/anthracenediones include, for example, doxorubicin, daunorubicin, epirubicin, and idarubicin. Epipodophyllotoxin derivatives include, for example, etoposide, etoposide phosphate and teniposide. Camptothecins include, for example, irinotecan, topotecan, 9-aminocamptothecin, 10,11-methylenedioxycamptothecin, karenitecin, 9-nitrocamptothecin, and TAS 103. Hormones and hormonal analogs may include, for example, estrogens and estrogen analogs, including anastrazole, diethylstilbesterol, estradiol, premarin, raloxifene; progesterone, progesterone analogs and progestins, including progesterone, norethynodrel, esthisterone, dimesthisterone, megestrol acetate, medroxyprogesterone acetate, hydroxyprogesterone caproate, and norethisterone; androgens, including fluoxymesterone, methyltestosterone and testosterone; as well as adrenocorticosteroids, including dexamthasone, prednisone, cortisol, solumedrol, and the like. Antihormones include, for example, (i) antiestrogens, including: tamoxifen, fulvestrant, toremifene; aminoglutethimide, testolactone, droloxifene, anastrozole; (ii) antiandrognes, including: bicalutamide, flutamide, nilutamide, goserelin; (iii) antitestosterones, including: flutamide, leuprolide, and triptorelin; (iv) adrenal steroid inhibitors including: aminoglutethimide and mitotane; and anti-leuteinizing hormones, including goserelin. Enzymes, proteins, peptides, polyclonal and/or monoclonal antibodies, may include, for example, asparaginase, cetuximab, erlotinib, bevacizumab, rituximab, gefitinib, trastuzumab, interleukins, interferons, leuprolide, pegasparanase, and the like. Vinca Alkaloids include, for example, vincristine, vinblastine, vinorelbine, vindesine, and the like. Taxanes include, for example, paclitaxel, docetaxel, and formulations and analogs thereof. Alkylating agents may include, for example, dacarbazine; procarbazine; temozolamide; thiotepa; nitrogen mustards (e.g., mechlorethamine, chlorambucil, L-phenylalanine mustard, melphalan, and the like); oxazaphosphorines (e.g., ifosphamide, cyclophosphamide, mefosphamide, perfosfamide, trophosphamide and the like); alkyl sulfonates (e.g., busulfan); and nitrosoureas (e.g., carmustine, lomustine, semustine and the like). Epothilones include, for example, epothilones A-E. Antimetabolites include, for example, tomudex and methotrexate, 6-mercaptopurine, and 6-thioguanine. Topoisomerase inhibitors include, for example, irinotecan, and topotecan, karenitecin, amsacrine, etoposide, etoposide phosphate, teniposide, and doxorubicin, daunorubicin, and other analogs. Antiviral agents include, for example, acyclovir, valacyclovir, ganciclovir, amantadine, rimantadine, lamivudine, and zidovudine. Monoclonal antibody agents include, for example, bevacizumab, trastuzumab, rituximab, and the like, as well as growth inhibitors such as erlotinib, and the like. In general, cytostatic agents are mechanism-based agents that slow the progression of neoplastic disease.

In one embodiment, the method further comprises one or more hydration step(s).

In one embodiment, the method further comprises one or more premedication(s).

In one embodiment, the method further comprises one or more hydration step(s) and one or more premedication(s).

In one embodiment, the method is carried out to treat one or more cancers in a subject. In another embodiment, the subject is a human. Cancers include all cancers and may include, for example, one or more cancers of the ovary, breast, lung, esophagus, bladder, stomach, pancreas, liver (including gall bladder and bile ducts, and Ampulla of Vater), testes, germ cell, bone, cartilage, head, neck, oral mucosa, colorectal area (including colon cancer), anus, kidney, uroepithelium, lymphoma, central nervous system, prostate, endometrium, cervix, uterus, fallopian tube, peripheral nervous system, as well as cancers such as melanoma, mesothelioma, myeloma, leukemia, and Kaposi's sarcoma.

SUMMARY OF FIGURES

FIG. 1 illustrates a comparison of the number of hypersensitivity Adverse Events between groups of patients in whom 2,2'-dithio-bis-ethane sulfonate or a placebo was infused over (1) 30 minutes, (2) 30 and 45 minutes, or (3) 45 minutes. The chemotherapeutic agent administered was paclitaxel. In this Figure, n=#, equals the number of patients.

FIG. 2 illustrates a comparison of the number of patients experiencing at least one drug-related (i.e., disodium 2,2'-dithio-bis-ethane sulfonate-related) Serious Adverse Event (SAE) and those patients experiencing at least one drug-related grade 3 or greater Adverse Event (AE) between groups of patients wherein disodium 2,2'-dithio-bis-ethane sulfonate was infused over 30 minutes, 30 and 45 minutes, or 45 minutes. Drug concentrations of disodium 2,2'-dithio-bis-ethane sulfonate administered were 200 mg/mL infused over 30 minutes, 200 mg/mL and 100 mg/mL infused over 30 & 45 minutes, respectively, and 100 mg/mL infused over 45 minutes. Drug-related Adverse Events are rated from grade 1 to grade 5 and relate to the severity or intensity of the Adverse Event (grade 1 is mild, grade 2 is moderate, grade 3 is severe, grade 4 is life threatening, and grade 5 results in death). A full definition of Adverse Events is provided, below. The chemotherapeutic agent administered was paclitaxel. In this Figure, n=#, equals the number of patients.

FIG. 3 illustrates, in tabular form, the Primary Endpoint, for the Japan Phase III Clinical Trial involving the mitigation or prevention of patient peripheral neuropathy as determined utilizing the utilizing the Peripheral Neuropathy Questionnaire (PNQ©). The results confirm the existence of an "intermittent" form of peripheral neuropathy, as well as the fact that it can be measured using the (PNQ©).

FIG. 4 illustrates data from the Japan Phase III Clinical Trial supporting the merit of utilizing the Patient Neurotoxicity Questionnaire (PNQ©) and the GEE (Generalized Estimating Equation) statistical method to measure patient peripheral neuropathy, consisting of intermittent and cumulative peripheral neuropathy.

FIG. 5 illustrates the reduction in peripheral neuropathy for the Tavocept™ or BNP7787 arm of the Japan Phase III Clinical Trial as compared to the placebo arm, indicating a lower level of severe peripheral neuropathy in the Tavocept™ arm of the Japan Phase III Clinical Trial.

DETAILED DESCRIPTION OF THE INVENTION

Definitions

"Scaffold" or "Skeleton" mean the fixed structural part of the molecule of the formula given.

"Nucleophile" means an ion or molecule that donates a pair of electrons to an atomic nucleus to form a covalent bond; the nucleus that accepts the electrons is called an electrophile. This occurs, for example, in the formation of acids and bases according to the Lewis concept, as well as in covalent carbon bonding in organic compounds.

"Pharmaceutically-acceptable salt" means salt derivatives of drugs which are accepted as safe for human administration. In the present invention, these derivatives may comprise various salts including, but not limited to, inorganic salts and alkaline earth metal salts.

"Fragments", "Moieties" or "Substituent Groups" are the variable parts of the molecule, designated in the formula by variable symbols, such as $R_x$, X or other symbols. Substituent Groups may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a straight or branched chain hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond (alkenyl) or triple bond (alkynyl) between two of the carbon atoms;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Amine" means a class of organic complexes of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contain from 1 to 10 carbon atoms;

"Azide" means any group of complexes having the characteristic formula $R(N_3)x$. R may be almost any metal atom, a hydrogen atom, a halogen atom, the ammonium radical, a complex [$CO(NH_3)_6$], [$Hg(CN)_2M$], (with M=Cu, Zn, Co, Ni) an organic radical like methyl, phenyl, nitrophenol, dinitrophenol, p-nitrobenzyl, ethyl nitrate, and the like. The azide group possesses a chain structure rather than a ring structure;

"Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Imine" means a class of nitrogen-containing complexes possessing a carbon-to-nitrogen double bond (i.e., R—CH=NH).

"Osmolarity" is a measure of the osmoles of solute per kilogram of solvent. For purposes of calculating osmolarity, salts are presumed to dissociate into their component ions. For example, a mole of glucose in solution is one osmole, whereas a mole of sodium chloride in solution is two osmoles (one mole of sodium and one mole of chloride). Both sodium and chloride ions affect the osmotic pressure of the solution. The equation to determine the osmolarity of a solution is given by $Osm = \Phi nC$, where $\Phi$ is the osmotic coefficient and accounts for the degree of dissociation of the solute; $\Phi$ is between 0 and 1, where 1 indicates 100% dissociation; n is the number of particles into which a molecule dissociates (for example: Glucose equals 1 and NaCl equals 2); and C is the molar concentration of the solution.

"Substituted" modifies the identified fragments (moieties) by replacing any, some or all of the hydrogen atoms with a moiety (moieties) as identified in the specification. Substitutions for hydrogen atoms to form substituted complexes include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

As used herein "chemotherapeutic agent" or "chemotherapy agent" or "antineoplastic agent" refer to an agent that reduces, prevents, mitigates, limits, and/or delays the growth of metastases or neoplasms, or kills neoplastic cells directly by necrosis or apoptosis of neoplasms or any other mechanism, or that can be otherwise used, in a pharmaceutically-effective amount, to reduce, prevent, mitigate, limit, and/or delay the growth of metastases or neoplasms in a subject with neoplastic disease. Chemotherapeutic agents include, for example, fluoropyrimidines; pyrimidine nucleosides; purine nucleosides; anti-folates, platinum complexes; anthracyclines/anthracenediones; epipodopodophyllotoxins; camptothecins; hormones; hormonal complexes; antihormonals; enzymes, proteins, and antibodies; vinca alkaloids; taxanes; antimirotubule agents; alkylating agents; antimetabolites; topoisomerase inhibitors; antivirals; and miscellaneous cytotoxic and cytostatic agents. "Chemotherapy" refers to treatments using chemotherapeutic agents, chemotherapy agents, or antineoplastic agents.

As used herein, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That outcome can be reduction, prevention, mitigation, delay, shortening the time to resolution of, alleviation of the signs or symptoms of, or exert a medically-beneficial effect upon the underlying pathophysiology or pathogenesis of an expected or observed Adverse Event, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; and/or an increase in duration of chemotherapeutic therapy.

As used herein, the term "platinum medicaments" or "platinum compounds" include all compounds, compositions, and formulations which contain a platinum ligand in the structure of the molecule. By way of non-limiting example, the valence of the platinum ligand contained therein may be platinum II or platinum IV. The platinum medicaments or platinum compounds of the present invention include, in a non-limiting manner, cisplatin, oxaliplatin, carboplatin, satraplatin, and analogs and derivatives thereof.

As used herein, the term "taxane medicaments" include, in a non-limiting manner, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof.

As used herein, the term "a medically sufficient dosage" in reference to the compounds or compositions of the instant invention refers to the dosage that is sufficient to induce a desired biological, pharmacological, or therapeutic outcome in a subject with need thereof.

As utilized herein, adenocarcinoma refers to a cancer that originates in glandular tissue. Glandular tissue comprises organs that synthesize a substance for release such as hormones. Glands can be divided into two general groups: (i) endocrine glands—glands that secrete their product directly onto a surface rather than through a duct, often into the blood stream and (ii) exocrine glands—glands that secrete their products via a duct, often into cavities inside the body or its outer surface. However, it should be noted that to be classified as adenocarcinoma, the tissues or cells do not necessarily need to be part of a gland, as long as they have secretory properties. Adenocarcinoma may be derived from various tissues including, but not limited to, breast, colon, lung, prostate, salivary gland, stomach, liver, gall bladder, pancreas (99% of pancreatic cancers are ductal adenocarcinomas), cervix, vagina, and uterus, as well as unknown primary adenocarcinomas. Adenocarcinoma is a neoplasm which frequently presents marked difficulty in differentiating from where and from which type of glandular tissue the tumor(s) arose. Thus, an adenocarcinoma identified in the lung may have had its origins (or may have metastasized) from an ovarian adenocarcinoma. Cancer for which a primary site cannot be found is called cancer of unknown primary.

As utilized herein, the term non-small cell lung cancer (NSCLC) accounts for approximately 75% of all primary lung cancers. NSCLC is pathologically characterized further into adenocarcinoma, squamous cell carcinoma, large cell carcinoma, and other less common forms. Clinically there are important differences in NSCLC that can be observed in smokers and non-smokers.

As used herein, the term "reducing" or "reduces" includes reducing, preventing, mitigating, delaying the onset of, attenuating the severity of, and/or hastening the resolution of a chemotherapy-associated Adverse Event, symptom, sign, or condition in a subject, including preventing the onset, or the development of more severe forms of an adverse symptom, sign, or condition in a subject, in whole or in part, or ameliorating or controlling such adverse forms of symptoms, signs, or conditions in the subject, as they involve any drug-related or chemotherapy-associated Adverse Events in the form of toxicities, Adverse Experiences, and/or Adverse Effects.

As used herein the terms "Adverse Event", "Adverse Effect", or "Adverse Experience" include a manifestation or condition that is reported by the patient (e.g., nausea, chills, depression, numbness, tingling, anorexia, dysguesia, and the like). An "adverse sign" means an objective finding that is a physically observable manifestation of a condition, Adverse Event in the patient (e.g., palpable purpura, maculopapular rash, spider angioma, Chvostek's sign, Babinski's sign, Trousseau's sign, opisthotonos, and the like).

Definitions for the terms Adverse Event (effect or experience), adverse reaction, and unexpected adverse reaction have previously been agreed to by consensus of the more than 30 Collaborating Centers of the WHO International Drug Monitoring Centre (Uppsala, Sweden). See, Edwards, I. R., et al., Harmonisation in Pharmacovigilance *Drug Safety* 10(2): 93-102 (1994). The following definitions, with input from the WHO Collaborative Centre, have been agreed to:

1. Adverse Event (Adverse Effect or Adverse Experience)—Any untoward medical occurrence in a patient or clinical investigation subject administered a pharmaceutical product and which does not necessarily have to have a causal relationship with this treatment. An Adverse Event (AE) can therefore be any unfavorable and unintended sign (including an abnormal laboratory finding, for example), symptom, or disease temporally associated with the use of a medicinal product, whether or not considered related to the medicinal product.

2. Adverse Drug Reaction (ADR)—In the pre-approval clinical experience with a new medicinal product or its new usages, particularly as the therapeutic dose(s) may not be established: all noxious and unintended responses to a medicinal product related to any dose should be considered adverse drug reactions. Drug-related Adverse Events are rated from grade 1 to grade 5 and relate to the severity or intensity of the event. Grade 1 is mild, grade 2 is moderate, grade 3 is severe, grade 4 is life threatening, and grade 5 results in the subject's death.

3. Unexpected Adverse Drug Reaction—An adverse reaction, the nature or severity of which is not consistent with the applicable product information.

Serious Adverse Event or Adverse Drug Reaction: A Serious Adverse Event (experience or reaction) is any untoward medical occurrence that at any dose:

(1) Results in death, Is life-threatening. It should be noted that the term "life-threatening" in the definition of "serious" refers to an event in which the patient was at risk of death at the time of the event; it does not refer to an event which hypothetically might have caused death if it were more severe.

(2) Requires inpatient hospitalization or prolongation of existing hospitalization.

(3) Results in persistent or significant disability/incapacity, or (4) Is a congenital anomaly/birth defect.

As used herein an "analog" of a compound refers to molecules that share substantial structural (e.g., scaffold or skeleton) and/or functional characteristics with the parent compound. For example, analogs of 2,2'-dithio-bis-ethanesulfonate may include, unless specifically identified otherwise, compounds of Formula (I); prodrugs thereof; pharmaceutically-acceptable salts of the compounds and/or prodrugs; and conjugates, hydrates or solvates of the compounds, salts and/or prodrugs; as well as stereoisomers (including diastereoisomers and enantiomers) and tautomers of the compounds, salts, and/or prodrugs.

As used herein a "solvate" of a compound refers to a molecular complex of the solute (the compound) and the solvent. For example, a solvate of the present invention may comprise of a molecular complex represented by Formula (I) compounds including, for example, 2,2'-dithio-bis-ethanesulfonate analogs, conjugates, hydrates, prodrugs, polymorphs, as well as stereoisomers (including diastereoisomers and enantiomers) and tautomers thereof, and pharmaceutically acceptable salts thereof, with one or more solvent molecules. Such solvent molecules are those that are commonly used in the pharmaceutical art, e.g., water, ethanol, and the like. The term "hydrate" refers to the molecular complex where the solvent molecule is water.

As used herein, the terms "Formula (I) compound" or "Formula (I) composition" include all molecules, unless specifically identified otherwise, that share substantial structural and/or functional characteristics with the 2,2'-dithio-bisethane sulfonate parent compound and includes the compounds of Formula (I) which refers to compounds possessing the generic structural formula:

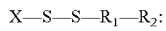

wherein;

$R_1$ is a lower alkylene, wherein $R_1$ is optionally substituted by a member of the croup comprising: lower alkyl, aryl, hydroxy, alkoxy, aryloxy, mercapto, alkylthio or arylthio, for a corresponding hydrogen atom, or

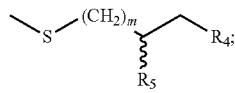

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide comprising from 2-10 amino acids; or wherein X is a member of the group comprising a: lower thioalkyl (lower mercapto alkyl), lower alkylsulfonate, lower alkylphosphonate, lower alkenylsulfonate, lower alkyl, lower alkenyl, lower alkynyl, acyl, alkoxy, aryloxy, mercapto, alkylthio or hydroxy for a corresponding hydrogen atom.

The Formula (I) compounds or compositions of the present invention also include pharmaceutically-acceptable salts, prodrugs, analogs, conjugates, hydrates, solvates, polymorphs, stereoisomers (including diastereoisomers and enantiomers) and tautomers thereof.

By way of non-limiting example, the Formula (I) compounds or compositions of the present invention include the disodium salt of 2,2'-dithio-bis-ethane sulfonate (which has also been referred to in the literature as dimesna, Tavocept™, and BNP7787). Additionally, by way of non-limiting example, the Formula (I) compounds or compositions of the present invention include the metabolite of disodium 2,2'-dithio-bis-ethane sulfonate, known as 2-mercapto ethane sulfonate sodium (also known in the literature as mesna) or 2-mercapto ethane sulfonate conjugated with a substituent group consisting of: -Cys, -Homocysteine, -Cys-Glu, -Cys-Glu-Gly, -Cys-Homocysteine, -Homocysteine-Gly, -Homocysteine-Glu, -Homocysteine-Glu-Gly, and -Homocysteine —$R_1$; wherein $R_1$, and $R_2$

are any L- or D-amino acid.

It should be noted that all of the aforementioned chemical entities and compounds in the previous two (2) paragraphs are included in Formula (I) compounds of the present invention. The compounds of Formula (I) include pharmaceutically-acceptable salts of such compounds, as well as prodrugs, analogs, conjugates, hydrates, solvates and polymorphs, as well as stereoisomers (including diastereoisomers and enantiomers) and tautomers of such compounds. Compounds of Formula (I), and their synthesis are described in e.g., U.S. Pat. Nos. 5,808,160, 5,922,902, 6,160,167, and 6,504,049; and Published U.S. Patent Application 2005/0256055, the are hereby incorporated by reference in their entirety.

As used herein, the term "pre-treatment" comprises the administration of one or more medications, said administration occurring at various times including: at least one day prior to chemotherapy, prior to each chemotherapy treatment, immediately prior to each chemotherapy treatment, concomitantly with or simultaneously during chemotherapy treatment, immediately subsequent to chemotherapy, subsequent to chemotherapy, and/or according to methods known within the art and in accordance with the patient's medical condition.

As used herein, the term "cytostatic agents" are mechanism-based agents that slow the progression of neoplastic disease.

As used herein the term "cytotoxic agents" are any agents or processes that kill neoplastic cells.

As used herein, "treatment schedule time" means the difference in schedule of administration time, including: (i) the amount of drug administered per week; (ii) the amount of drug administered per week/per $m^2$ of body surface area; and (iii) the amount of drug administered per week per kg of body weight.

The descriptions and embodiments set forth herein are not intended to be exhaustive, nor do they limit the invention to the precise forms disclosed. They are included to illustrate the principles of the invention, and its application and practical use by those skilled in the art.

2,2'-dithio-bis-ethane sulfonate has previously been shown to be useful in enhancing the utility of chemotherapeutic agents. See, Published U.S. Patent Application 2003/0203960, Published U.S. Patent Application No. 2003/0133994, U.S. Pat. No. 5,902,610, and U.S. Pat. No. 5,789,000.

New methods of administration of agents such as 2,2'-dithio-bis-ethane sulfonate, pharmaceutically-acceptable salts, and/or an analog thereof, have now been discovered in connection with a human clinical study comprising a randomized, double-blind, placebo-controlled study with a 1:1 randomization. Initial blinded study results support the ability of compounds such as 2,2'-dithio-bis-ethane sulfonate to markedly enhance overall safety, decrease overall Adverse Events, decrease hypersensitivity-based Adverse Events, and increase the time of Adverse Event onset, while maintaining at least the same therapeutic indices (e.g. dose level administered in a prescribed specific time schedule, including duration of administration and frequency), and reduction, prevention, mitigation, and/or delay of toxicities associated with the administration of chemotherapeutic agents.

Clinical study results support the administration of compounds such as 2,2'-dithio-bis-ethane sulfonate, pharmaceutically-acceptable salts thereof, and/or analogs thereof, over a period of about 45 minutes and at a concentration of about 100 mg/mL, which resulted in an observed substantial decrease in the frequency and severity of hypersensitivity Adverse Events over previously disclosed methods of administration. For example, as shown in FIG. 1, the proportion of patients with at least one hypersensitivity Adverse Event was lowered from approximately 42% to approximately 30%. These results are based upon a double-blind, placebo-controlled study with a 1:1 randomization; which includes patients who received placebo, as well as all patients in cohorts treated with paclitaxel, which is known to produce hypersensitivity reactions and more severe forms of allergic reactions including anaphylaxis. It is noted that the overall expected value for paclitaxel alone is approximately 40-45% hypersensitivity reactions; however a reduction in the overall proportion of patients experiencing hypersensitivity reactions by approximately 12% (i.e., approximately 42% to approximately 30%) was observed. This reduction in the proportion of patients experiencing hypersensitivity reactions overall represents a medically significant difference in such adverse reactions. It represents a reduction in the risk of an observed potentially serious and life-threatening Adverse Event by approximately 29% in the entire study population (i.e., both placebo and 2,2'-dithio-bis-ethane sulfonate populations). As there is no additive or expected placebo induced-effect affecting reported hypersensitivity Adverse Events, there may be up to an approximate 57% reduction in such hypersensitivity Adverse Events in the 2,2'-dithio-bis-ethane sulfonate treatment population (e.g., approximately 42% observed overall, prior to the implementation of novel methods of administration to which the present invention relates, followed by approximately 30% observed incidence, after such implementation). In the aforementioned calculations, approximately 42% represents the incidence of hypersensitivity Adverse Events observed or reported in the entire treated population who received paclitaxel plus either placebo or 2,2'-dithio-bis-ethane sulfonate (i.e., 1:1 or approximately 50%, each) at 200 mg/mL over a total of 30 minutes; whereas approximately 30% represents the incidence of hypersensitivity Adverse Events observed or reported in the entire treated population who received paclitaxel plus either placebo or 2,2'-dithio-bis-ethane sulfonate (i.e., 1:1 or approximately 50% each) at 100 mg/mL over a total of 45 minutes.

Results similar to that found in FIG. 1 were shown in FIG. 2, with an observed substantial decrease in the frequency of drug-related (i.e., disodium 2,2'-dithio-bis-ethane sulfonate-related) Serious Adverse Events with the administration of disodium 2,2'-dithio-bis-ethane sulfonate over about 45 minutes and at a concentration of about 100 mg/mL when compared to an administration period of about 30 minutes at a concentration of about 200 mg/mL. The 45 minute administration of a compound with a concentration of 100 mg/mL resulted in the proportion of patients experiencing at least one drug-related Serious Adverse Event (SAE) being lowered from approximately 7.6% to approximately 5.4%, an approximate 29% overall reduction. Moreover, the percentage of patients experiencing at least one drug-related Adverse Event of grade 3 or higher was decreased from 16.4% (30 minutes, 200 mg/mL) to 8.6% (45 minutes, 100 mg/mL), an approximate 47% overall reduction.

The invention includes methods, formulations, and devices. The methods, formulations, and devices may be used for reducing, preventing, mitigating, delaying the onset of, attenuating the severity of, and/or hastening the resolution of toxicity in a subject receiving a chemotherapeutic agent comprising administering to the subject, an effective amount of a 2,2'-dithio-bis-ethane sulfonate, a pharmaceutically-acceptable salt thereof, and/or an analog thereof, which include the compounds of Formula (I).

The invention additionally involves the use of the methods and the administration of the compositions and formulations described herein to a subject, optionally with or within a device, wherein the administration takes place as medically indicated in the subject prior to, concurrently or simultaneously, or following the administration of any chemotherapeutic agent or pharmaceutically active compound(s) associated with any one or more of the toxicities noted herein by any route, dose, concentration, duration or schedule.

Various chemotherapeutic agents may be used in conjunction with, or as a part of, the methods described and claimed herein. Chemotherapeutic agents may include, for example, a fluoropyrimidine; a pyrimidine nucleoside; a purine nucleoside; an antifolate, a platinum analog; an anthracycline/anthracenedione; an epipodophyllotoxin; a camptothecin; a hormone, a hormonal analog; an antihormonal; an enzyme, protein, peptide, or polyclonal and monoclonal antibody; a vinca alkaloid; a taxane; an epothilone; an antimicrotubule agent; an alkylating agent; an antimetabolite; a topoisomerase inhibitor; an antiviral; or another cytotoxic and/or cytostatic agent.

Fluoropyrimidines may include, for example, 5-fluorouracil (5-FU), S-1 capecitabine, ftorafur, 5'deoxyfluorouridine, UFT, eniluracil, and the like.

Pyrimidine nucleosides may include, for example, cytarabine, deoxycytidine, 5-azacytosine, gemcitabine, 5-azadeoxycytosine, and the like.

Purine nucleosides may include, for example, fludarabine, 6-mercaptopurine, thioguanine, allopurinol, cladribine, 2-chloro adenosine, and the like.

Antifolates may include, for example, methotrexate (MTX), trimetrexate, aminopterin, methylene-10-deazaminopterin (MDAM), and the like.

Platinum analogs may include, for example, cisplatin, carboplatin, oxaplatin, picoplatin, tetraplatin, satraplatin, platinum-DACH, ormaplatin, CI-973, JM-216, and analogs thereof.

Anthracyclines/anthracenediones may include, for example, doxorubicin, daunorubicin, epirubicin, idarubicin, and the like.

Epipodophyllotoxin derivatives may include, for example, etoposide, etoposide phosphate, teniposide, and the like.

Camptothecins may include, for example, irinotecan, topotecan, 9-aminocamptothecin, 10,11-methylenedioxycamptothecin, karenitecin, 9-nitrocamptothecin, TAS 103, and the like.

Hormones and hormonal analogs may include, for example, estrogens and estrogen analogs, including anastrazole, diethylstilbesterol, estradiol, premarin, raloxifene; progesterone, progesterone analogs and progestins, including progesterone, norethynodrel, esthisterone, dimesthisterone, megestrol acetate, medroxyprogesterone acetate, hydroxyprogesterone caproate, and norethisterone; androgens, including fluoxymesterone, methyltestosterone and testosterone; adrenocorticosteroids, including dexamthasone, prednisone, cortisol, solumedrol, and the like.

Antihormones, may include, for example, antiestrogens (e.g., tamoxifen, fulvestrant, toremifene, aminoglutethimide, testolactone, droloxifene, anastrozole); antiandrogens (e.g., bicalutamide, flutamide, nilutamide, goserelin); antitestosterones (e.g., flutamide, leuprolide, triptorelin); adrenal steroid inhibitors (e.g., aminoglutethimide and mitotane); and antileuteinizing hormones (e.g., goserelin).

Enzymes, proteins, peptides, polyclonal and/or monoclonal antibodies may include, for example, asparaginase, cetuximab, erlotinib, bevacizumab, rifuximab, trasfuzumab, gefitinib, interleukins, interferons, leuprolide, pegasparanase, and the like.

Vinca alkaloids may include, for example, vincristine, vinblastine, vinorelbine, vindesine, and the like.

Taxanes may include, for example, paclitaxel, docetaxel, and various formulations and analogs thereof.

Alkylating agents may include, for example, dacarbazine; procarbazine; temozolamide; thiotepa; nitrogen mustards (e.g., mechlorethamine, chlorambucil, L-phenylalanine mustard, melphalan, and the like); oxazaphosphorines (e.g., ifosphamide, cyclophosphamide, mefosphamide, perfosfamide, trophosphamide and the like); alkyl sulfonates (e.g., busulfan); and nitrosoureas (e.g., carmustine, lomustine, thiotepa, semustine and the like).

Epothilones may include, for example, epothilones A-E, and the like.

Antimetabolites may include, for example, tomudex, methotrexate, 6-mercaptopurine, 6-thioguanine, and the like.

Topoisomerase inhibitors may include, for example, irinotecan, topotecan, amsacrine, etoposide, etoposide phosphate, teniposide, doxorubicin, daunorubicin, karenitecin, and various other analogs.

Antiviral agents may include, for example, acyclovir, valacyclovir, ganciclovir, amantadine, rimantadine, lamivudine, zidovudine, and the like.

Cytostatic agents, such as monoclonal antibodies, may include, for example, bevacizumab, trastuzumab, rituximab, and the like.

Formula (I) refers to the compounds:

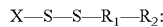

wherein;

$R_1$ is a lower alkylene, wherein $R_1$ is optionally substituted by a member of the group consisting of: aryl, hydroxy, alkoxy, aryloxy, mercapto, alkylthio or arylthio, for a corresponding hydrogen atom;

$R_2$ is sulfonate or phosphonate;

X is a sulfur-containing amino acid or a peptide consisting of from 2-10 amino acids; wherein X is optionally substituted by a member of the group consisting of: lower alkyl, lower alkenyl, lower alkynyl, aryl, alkoxy, aryloxy, mercapto, alkylthio or hydroxy for a corresponding hydrogen atom. The compounds of Formula (I) include pharmaceutically-acceptable salts thereof, as well as prodrugs, analogs, conjugates, hydrates, solvates and polymorphs, as well as stereoisomers (including diastereoisomers and enantiomers) and tautomers thereof. Compounds of Formula (I), and their synthesis are described in published U.S. Patent Application No. US 2005/0256055, the disclosure of which is hereby incorporated by reference in its entirety.

In one embodiment, an effective amount of 2,2'-dithio-bis-ethane sulfonate, a pharmaceutically-acceptable salt thereof, and/or an analog thereof, may include, for example, a range from about 0.01 $g/m^2$ to about 100 $g/m^2$. Additional effective doses may include, for example, from about 0.1 $g/m^2$ to about 90 $g/m^2$; about 1.0 $g/m^2$ to about 80 $g/m^2$; about 4.0 $g/m^2$ to about 70 $g/m^2$; about 5.0 $g/m^2$ to about 60 $g/m^2$; about 10 $g/m^2$ to about 50 $g/m^2$; about 15 $g/m^2$ to about 25 $g/m^2$; about 4 $g/m^2$, about 8 $g/m^2$; about 12 $g/m^2$; about 18 $g/m^2$; about 28 $g/m^2$; about 35 $g/m^2$; and about 41 $g/m^2$. Other amounts within these ranges may also be used.

In one preferred embodiment, 2,2'-dithio-bis-ethane sulfonate, a pharmaceutically-acceptable salt thereof, and/or an analog thereof, is administered at a concentration of about 100 mg/mL. In another preferred embodiment 2,2'-dithio-bis-ethane sulfonate, a pharmaceutically-acceptable salt thereof, and/or an analog thereof, is infused over about 45 minutes. In yet another preferred embodiment 2,2'-dithio-bis-ethane sulfonate, a pharmaceutically-acceptable salt thereof, and/or an analog thereof, is administered at a concentration of about 100 mg/mL over a period of about 45 minutes.

In another embodiment, 2,2'-dithio-bis-ethane sulfonate, a pharmaceutically-acceptable salt thereof, and/or an analog thereof, may be administered, for example, at an infusion rate of about 0.1 g/min. to about 4.6 g/min. Additional infusion rates include, for example, about 0.2 g/min to about 2.0 g/min.; about 0.2 g/min. to about 4.0 g/min.; about 0.25 g/min. to about 3.0 g/min., about 0.3 g/min. to about 2.5 g/min.; about 0.35 g/min. to about 2.0 g/min.; about 0.4 g/min. to about 1.5 g/min.; about 0.45 g/min. to about 1.4 g/min.; about 0.5 g/min. to about 1.3 g/min.; about 0.55 g/min. to about 1.3 g/min.; about 0.6 g/min. to about 1.2 g/min.; about 0.55 g/min. to about 1.2 g/min.; about 0.6 g/min. to about 1.1 g/min.; about 0.65 g/min. to about 1.0 g/min. Other amounts within these ranges may also be used.

The infusion rate can be calculated by those skilled in the art based on the desired dose per mass, Body Surface Area (BSA) of the subject and infusion time. For example, a dose of about 18.4 $g/m^2$, in a patient with a BSA of 1.7 $m^2$, infused over 45 minutes would have an infusion rate of about 0.7 g/minute.

In another embodiment, 2,2'-dithio-bis-ethane sulfonate, a pharmaceutically-acceptable salt thereof, and/or an analog thereof, is administered, for example, at about 1.0 mg/mL/min. to about 50 mg/mL/min. Additional dosing may include, for example, from about 2.0 mg/mL/min. to about 20 mg/mL/min.; about 1.5 mg/mL/min. to about 40 mg/mL/min.; about 2.0 mg/mL/min. to about 35 mg/mL/min.; about 2.5 mg/mL/min. to about 30 mg/mL/min.; about 3.0 mg/mL/min. to about 25 mg/mL/min.; about 3.5 mg/mL/min. to about 20 mg/mL/min.; about 4.0 mg/mL/min. to about 15 mg/mL/min.; about 4.5 mg/mL/min.; about 5.0 mg/mL/min.; about 5.5 mg/mL/min.; about 6.0 mg/mL/min.; about 6.5 mg/mL/min.; about 7.0 mg/mL/min.; about 7.5 mg/mL/min.; about 8.0 mg/mL/min.; about 8.5 mg/mL/min.; about 9.0 mg/mL/min.; about 9.5 mg/mL/min.; about 10 mg/mL/min.; about 11 mg/mL/min.; about 12 mg/mL/min.; about 13 mg/mL/min.; and about 14 mg/mL/min. Other amounts approximating these ranges may also be utilized. The mg/mL/min dosing schedule can be calculated by those skilled in the art based on a desired dose per mass, BSA of the subject, infusion time and desired concentration. For example, a dose of about 18.4 g/m2, in a patient with a BSA of about 1.7 $m^2$, infused over 45 minutes at a concentration of 100 mg/mL would be about 7 mg/mL/min.

In a preferred embodiment, the method of administration comprises administration of 2,2'-dithio-bis-ethane sulfonate, a pharmaceutically-acceptable salt thereof, and/or an analog thereof, in a composition that is hyperosmotic relative to the patient's plasma or serum osmolarity. In one embodiment, for example, the compound is administered in a composition having an osmolarity of about 0.1- to about 5-times the osmolarity of the normal plasma or serum osmolarity in a subject. In another embodiment, the compound is administered in a composition having an osmolarity of about 2- to about 4-times the osmolarity of the normal plasma or serum osmolarity in a subject. In yet other embodiments, the compound is administered in a composition having an osmolarity of about 1-; about 2-; about 3-; about 4-; or about 5-times the osmolarity of the normal plasma or serum osmolarity in a subject. The normal range of human plasma osmolarity ranges from approximately 280 mOsm to approximately 320 mOsm.

Without wishing to be bound by theory, hyperosmotic compositions are believed to facilitate a protective renal effect by inducing increases in renal clearance of body water, by an osmotically-mediated increase in the clearance of free water, thereby enhancing the rate, volume and/or frequency of urinary output per unit of time (i.e., diuresis). In addition, this hyperosmotic effect is believed to facilitate the entry of a chemoprotective agent, e.g., a 2,2'-dithio-bis-ethane sulfonate, a pharmaceutically-acceptable salt thereof, and/or an analog thereof, into cells, or conversely, an egress of free water from the intracellular compartment into the renal tubular lumen and collecting ducts, either by, for example, uptake of the agent by renal cells or osmotic diffusion of water in the tubular lumen of the kidney mediated by a process similar to the diffusion of a solute through a semi-permeable membrane (i.e., Le Chatea's diffusion principle). 2,2'-dithio-bis-ethane sulfonate, a pharmaceutically-acceptable salt thereof, and/or an analog thereof, may also be taken up by renal tubular epithelium by energy-dependent transport mechanisms, and thereby exert its beneficial biological, pharmaceutical and medicinal effects locally.

2,2'-dithio-bis-ethane sulfonate is a known compound and can be manufactured by methods known in the art. See, e.g., *J. Org. Chem.* 26:1330-1331 (1961); *J. Org. Chem.* 59:8239 (1994). In addition, 2,2'-dithio-bis-ethane sulfonate and other dithioethers may also be synthesized as outlined in U.S. Pat. No. 5,808,160, U.S. Pat. No. 6,160,167 and U.S. Pat. No. 6,504,049. Compounds of Formula (I) may be manufactured as described in U.S. Patent Application 2005/0256055.

In another embodiment of the invention, the 2,2'-dithio-bis-ethane sulfonate and/or an analog thereof, is a pharmaceutically-acceptable disodium salt. In other embodiments, the 2,2'-dithio-bis-ethane sulfonate and/or an analog thereof, is/are pharmaceutically-acceptable salt(s) which include, for example: (i) monosodium 2,2'-dithio-bis-ethane sulfonate; (ii) sodium potassium 2,2'-dithio-bis-ethane sulfonate; (iii) dipotassium 2,2'-dithio-bis-ethane sulfonate; (iv) calcium 2,2'-dithio-bis-ethane sulfonate; (v) magnesium 2,2'-dithio-bis-ethane sulfonate; (vi) manganese 2,2'-dithio-bis-ethane sulfonate; (vii) ammonium 2,2'-dithio-bis-ethane sulfonate; and (viii) monopotassium 2,2'-dithio-bis-ethane sulfonate. Mono- and di-potassium salts of 2,2'-dithio-bis-ethane sulfonate and/or an analog thereof are administered to a subject if the total dose of potassium administered at any given point in time is not greater than 100 Meq. and the subject is not hyperkalemic and does not have a condition that would predispose the subject to hyperkalemia (e.g., renal failure).

In one embodiment, the method of administration further comprises the step of administering one or more chemotherapeutic agents. The administration of a 2,2'-dithio-bis-ethane sulfonate, a pharmaceutically-acceptable salt thereof, and/or an analog thereof, may be prior to, immediately prior to, during, immediately subsequent to or subsequent to the administration of the one or more chemotherapeutic agents.

Chemotherapeutic agents may be prepared and administered to subjects using methods known within the art. For example, paclitaxel may be prepared using methods described in U.S. Pat. Nos. 5,641,803, 6,506,405, and 6,753,006 and is administered as known in the art (see, for example, U.S. Pat. Nos. 5,641,803, 6,506,405, and 6,753,006). Paclitaxel may be prepared for administration in a dose in the range of about 50 mg/m$^2$ and about 275 mg/m$^2$. Preferred doses include about 80 mg/m$^2$, about 135 mg/m$^2$ and about 175 mg/m$^2$.

Docetaxel may be prepared using methods described in U.S. Pat. No. 4,814,470 and is administered as known in the art (see, for example, U.S. Pat. Nos. 4,814,470, 5,438,072, 5,698,582, and 5,714,512). Docetaxel may be prepared for administration in a dose in the range of about 30 mg/m$^2$ and about 100 mg/m$^2$. Preferred doses include about 55 mg/m$^2$, about 60 mg/m$^2$, about 75 mg/m$^2$, and about 100 mg/m$^2$.

Cisplatin may be prepared using methods described in U.S. Pat. Nos. 4,302,446, 4,322,391, 4,310,515, and 4,915,956 and is administered as known in the art (see, for example, U.S. Pat. Nos. 4,177,263, 4,310,515, 4,451,447). Cisplatin may be prepared for administration in a dose in the range of about 30 mg/m$^2$ and about 120 mg/m$^2$ in a single dose or 15 mg/m$^2$ and about 20 mg/m$^2$ daily for five days. Preferred doses include about 50 mg/m$^2$, about 75 mg/m$^2$ and about 100 mg/m$^2$.

Carboplatin may be prepared using methods described in U.S. Pat. No. 4,657,927 and is administered as known in the art (see, for example, U.S. Pat. No. 4,657,927). Carboplatin may be prepared for administration in a dose in the range of about 20 mg/kg and about 200 mg/kg. Preferred doses include about 300 mg/m$^2$ and about 360 mg/m$^2$. Other dosing may be calculated using a formula according to the manufacturer's instructions.

Oxaliplatin may be prepared using methods described in U.S. Pat. Nos. 5,290,961, 5,420,319, 5,338,874 and is administered as known in the art (see, for example, U.S. Pat. No. 5,716,988). Oxaliplatin may be prepared for administration in a dose in the range of about 50 mg/m$^2$ and about 200 mg/m$^2$. Preferred doses include about 85 mg/m$^2$ and about 130 mg/m$^2$.

In another embodiment the method comprises one or more additional hydration step(s). Hydration comprises the administration of various fluids to the subject in need thereof for purposes of facilitating medical treatment to said subject. Such hydration may serve, e.g., to replace or increase internal fluid levels. For example, saline hydration may include administration of about 250 mL to about 1000 mL of 0.9% saline solution administered over about 1 hour to about 2 hours. Other forms of hydration, including hypertonic (e.g., 3% sodium chloride) or hypotonic (e.g., 0.45 M sodium chloride or Dextrose 5% in Water or Ringer's lactate) solutions that are commercially available for parenteral administration may be used in lieu of, or in combination with, or in addition to saline hydration as dictated by the patient's medical condition.

In another embodiment the method comprises an additional step of administering one or more pre-therapy medication(s). Pre-medications include, for example, antihistamines, steroids, antimetics, and 5-HT3 antagonists. Antihistamines may include, for example, diphenhydramine, clemastine, cimetidine, ranitidine and famotidine. Steroids may include, for example, corticosteroids, including hydrocortisone, dexamethasone, prednisolone and prednisone. Antiemetics may include, for example, prochloroperazine, metoclopramide, and dimenhydrinate. 5-HT3 antagonists may include, for example, ondansetron, dolasetron, and granisetron. Other pre-therapy drugs may include, for example, diazepam congeners, gabapentin and amitryptiline. Pre-therapy may be administered at least one day prior to chemotherapy, prior to each chemotherapy treatment, immediately prior to each chemotherapy treatment, concomitantly with or simultaneously during chemotherapy treatment, immediately subsequent to chemotherapy, subsequent to chemotherapy, and/or according to methods known within the art and in accordance with the patient's medical condition.

In one embodiment, 2,2'-dithio-bis-ethane sulfonate, a pharmaceutically-acceptable salt thereof, and/or an analog thereof, is administered to a subject in need of treatment for one or more cancers. Said subject may be a human. Said cancer or cancers may be human cancers, which may include, for example, one or more cancers of the: ovary, breast, lung, esophagus, bladder, stomach, pancreas, liver (e.g., bile ducts, gall bladder, and Ampulla of Vater), testes, germ cell, bone, cartilage, head, neck, oral mucosa, colorectal area, anus, kidney, uroepithelium, lymphoma, central nervous system, prostate, endometrium, cervix, uterus, fallopian tube, peripheral nervous system, and various other cancers including melanoma, mesothelioma, myeloma, leukemia, and Kaposi's sarcoma.

Aspects of the present invention also include controlled or other doses, dosage forms, formulations, compositions and/or devices containing 2,2'-dithio-bis-ethane sulfonate, a pharmaceutically-acceptable salt thereof, and/or an analog thereof, for example, doses and dosage forms for oral administration (for example by means of tablets, troches, lozenges, sublingual absorption, and the like), injection (for example: subcutaneous administration, intradermal administration, subdermal administration, intramuscular administration, depot administration, intravenous administration or intra-arterial administration, intra-cavitary administration (e.g., administration into the intrapleural or intraperitoneal space), and any such administration may occur by, for example, delivery via parenteral bolus, slow intravenous injection, and intravenous drip, as well as by the use of infusion devices (e.g., implantable infusion devices, both active and passive).

The dosage forms, formulations, devices and/or compositions of the invention may be formulated for periodic administration, including at least once daily administration, at least about once every two days, at least about once every three days, at least about once every four days, at least about once every five days, at least about once every six days, at least about once a week, at least about once every 1.5 weeks or less, at least about once every 2 weeks or less, at least about once every 2.5 weeks or less, at least about once every 3 weeks or less, at least about once every 3.5 weeks or less, at least about once every 4 weeks or less, at least about once every 5 weeks or less, or any time interval between one day and five weeks or more than once every five weeks.

In a preferred embodiment, the composition of the invention comprises 2,2'dithio-bis-ethane sulfonate, a pharmaceutically-acceptable salt thereof, and/or an analog thereof, at about 100 to about 200 mg/mL or, alternately, about 600 to about 1,800 mOsm/L.

In certain of the methods of the invention, and the uses of the compositions and formulations of the invention, the chemoprotective agent may be administered in conjunction with a chemotherapeutic agent wherein the duration of treatment comprises at least 3 continuous courses, each course being of a specified period for medication of a chemotherapeutic agent, for example, a taxane antineoplastic agent, and an interval for suspending the chemotherapeutic agent medication. In conjunction with the inventions described and claimed herein, the chemotherapeutic agent treatment may comprise, for example, 2 or more treatment courses, 5 or more treatment courses, 6 or more treatment courses, 7 or more treatment courses, 8 or more treatment courses, or 9 or more treatment courses. The treatment courses may also be continuous. The chemotherapeutic agent may be a taxane antineoplastic agent, such as paclitaxel or docetaxel. The chemotherapeutic agent, which may be a taxane antineoplastic agent such as paclitaxel or docetaxel, may also be administered in a course of therapy in combination with another chemotherapeutic agent, for example, a platinum analog antineoplastic drug. The platinum analog antineoplastic drug, for example, may be cisplatin, carboplatin, oxaliplatin, or satraplatin.

The compositions and formulations of the invention, alone or in combination with one or more chemotherapeutic agents, and instructions for their use, may be included in a form of packs or kits. Thus, the invention also includes kits comprising the compositions, formulations, and/or devices described herein with instructions for use. For example, a kit may comprise a 2,2'-dithio-bis-ethane sulfonate, a pharmaceutically-acceptable salt thereof, and/or an analog thereof and instructions for administration. Kits may additionally comprise one or more chemotherapeutic agents with instructions for their use. Kits may also additionally comprise one or more pre-treatments as described herein and instructions for their use.

In general, the compositions and formulations of the invention are administered once a day wherein a chemotherapeutic agent is administered at 1 day to 5 week intervals, or any times in between, or longer than 5 week intervals as described herein, and the compositions and formulations of the invention are administered on the same date as the chemotherapeutic agent is administered.

For example, a course of therapy may include a single dose of paclitaxel (175 mg/m$^2$) administered intravenously over 3 hours, pre-cisplatin saline hydration for 1 hour, immediately followed by a single dose of a 2,2'-dithiobis ethane sulfonate (in a formulation having the concentration and/or osmolarity set forth herein, and/or administered at a rate set forth herein) administered intravenously over about 45 minutes, a single dose of cisplatin (75 mg/m$^2$) administered intravenously over 1 hour and subsequently post-cisplatin saline hydration for 1.5 hours. This is but one example. The methods of the invention may be carried out, and the formulations of the invention used, with only one chemotherapeutic agent, e.g., a taxane or a platinum analog chemotherapeutic agent, or with more than one chemotherapeutic agent.

As noted herein, the methods of the invention may also be carried out, and the formulations of the invention also used, in conjunction with one or more premedications.

Pre-therapy may be administered at least one day prior to chemotherapy, prior to each chemotherapy treatment, immediately prior to each chemotherapy treatment, concomitantly with or simultaneously during chemotherapy treatment, immediately subsequent to chemotherapy, subsequent to chemotherapy, and/or according to methods known within the art and in accordance with the patient's medical condition. Premedications may be administered according to the manufacture's instructions. See also, e.g., Example 4, below.

Saline hydration may include, for example administration of about 250 mL to about 1000 mL of 0.9% saline solution administered over about 1 hour to about 2 hours. Other forms of hydration, including hypertonic (e.g., 3% sodium chloride) or hypotonic (e.g., 0.45 M sodium chloride or Dextrose 5% in Water or Ringer's lactate) solutions that are commercially available for parenteral administration may be used in lieu of, or in combination with, or in addition to saline hydration as dictated by the patient's medical condition. Hydration steps can be added prior to the administration of paclitaxel, after administration of 2,2'-dithio-bis-ethane sulfonate (or prodrugs, analogs, conjugates, hydrates, solvates, or polymorphs, as well as stereoisomers (including diastereoisomers and enantiomers) and tautomers thereof)), prior to the administration of cisplatin, and/or after the administration of cisplatin.

Examples of dosage of forms suitable for injection of the compounds and formulations of the invention include delivery via bolus such as single or multiple or continuous or constant administrations by intravenous injection, subcutaneous, subdermal, and intramuscular administration. These forms may be injected using syringes, pens, jet injectors, and internal or external pumps, with vascular or peritoneal access, for example. Syringes come in a variety sizes including 0.3, 0.5, 1, 2, 5, 10, 25 and 50 mL capacity. Needleless jet injectors are also known in the art and use a pressurized air to inject a fine spray of solution into the skin. Pumps are also known in the art. The pumps are connected by flexible tubing to a catheter, which is inserted into the tissue just below the skin. The catheter is left in place for several days at a time. The pump is programmed to dispense the necessary amount of solution at the proper times. In addition, the invention provides for infusion dose delivery formulations and devices, including but not limited to implantable infusion devices for delivery of compositions and formulations of the invention. Implantable infusion devices may also comprise a coating of, or a portion of, a medical device wherein the coating comprises the polymer loaded with 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)).

Examples of infusion devices for compounds and formulations of the invention include infusion pumps containing a 2,2'-dithio-bis-ethane sulfonate, a pharmaceutically-acceptable salt thereof, and/or an analog thereof, to be administered at a desired rate and amount for a desired number of doses or steady state administration, and include implantable drug pumps.

Examples of implantable infusion devices for compounds, and formulations of the invention include any solid form or liquid form in which the active agent is a solution, suspension or encapsulated within or dispersed throughout a biodegradable polymer or synthetic polymer, for example, silicone, polypropylene, silicone rubber, silastic or similar polymer.

Examples of controlled drug formulations useful for delivery of the compounds and formulations of the invention are found in, for example, Sweetman, S. C. (Ed.)., *The Complete Drug Reference*, 33rd Edition, Pharmaceutical Press, Chicago, 2483 pp. (2002); Aulton, M. E. (Ed.), *Pharmaceutics: The Science of Dosage Form Design*. Churchill Livingstone, Edinburgh, 734 pp. (2000); and, Ansel, H. C., Allen, L. V. and Popovich, N. G., *Pharmaceutical Dosage Forms and Drug Delivery Systems*, 7th Ed., Lippincott, 676 pp. (1999). Excipients employed in the manufacture of drug delivery systems are described in various publications known to those skilled in the art including, for example, Kibbe, E. H., *Handbook of Pharmaceutical Excipients*, 3rd Ed., American Pharmaceutical Association, Washington, 665 pp. (2000).

Further examples of dosage forms of the invention include, but are not limited to modified-release (MR) dosage forms including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, however these terms may be applicable to any of the dosage forms, formulations, compositions and/or devices described herein. These formulations effect delayed and controlled total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

Modified-release dosage forms of the invention include dosage forms having drug release features based on time, course, and/or location which are designed to accomplish therapeutic or convenience objectives not offered by conventional or immediate-release forms. See, e.g., Bogner, R. H., Bioavailability and bioequivalence of extended-release oral dosage forms. *U.S. Pharmacist* 22 (*Suppl.*):3-12 (1997). Extended-release dosage forms of the invention include, for example, as defined by The United States Food and Drug Administration (FDA), a dosage form that allows a reduction in dosing frequency to that represented by a conventional dosage form, e.g., a solution or an immediate-release dosage form.

The present invention provides extended-release formulations containing 2,2'-dithio-bis-ethane sulfonate, a pharmaceutically-acceptable salt thereof, and/or analogs thereof, for parenteral administration. Extended rates of 2,2'-dithio-bis-ethane sulfonate, a pharmaceutically-acceptable salt thereof, and/or an analog thereof, action following injection may be achieved in a number of ways, including the following: crystal or amorphous 2,2'-dithio-bis-ethane sulfonate forms having prolonged dissolution characteristics; slowly dissolving chemical complexes of the 2,2'-dithio-bis-ethane sulfonate formulation; solutions or suspensions of 2,2'-dithio-bis-ethane sulfonate, a pharmaceutically-acceptable salt thereof, and/or an analog thereof, in slowly absorbed carriers or vehicles (e.g., oleaginous); increased particle size of 2,2'-dithio-bis-ethane sulfonate, a pharmaceutically-acceptable salt thereof, and/or analogs thereof, in suspension; or, by injection of slowly eroding microspheres of 2,2'-dithio-bis-ethane sulfonate, a pharmaceutically-acceptable salt thereof, and/or an analog thereof, (see, e.g., Friess, W., Lee, G. and Groves, M. J., Insoluble collagen matrices for prolonged delivery of proteins. *Pharmaceut. Dev. Technol.* 1:185-193 (1996). For example, the duration of action of the various forms of insulin is based in part on its physical form (amorphous or crystalline), complex formation with added agents, and its dosage form (solution of suspension).

An acetate, phosphate, citrate, bicarbonate, glutamine or glutamate buffer may be added to modify pH of the final composition. Optionally a carbohydrate or polyhydric alcohol tonicifier and, a preservative selected from the group consisting of m-cresol, benzyl alcohol, methyl, ethyl, propyl and butyl parabens and phenol may also be added. Water for injection, tonicifying agents such as sodium chloride, as well as other excipients, may also be present, if desired. For parenteral administration, formulations may be isotonic or substantially isotonic to avoid irritation and pain at the site of administration. Alternatively, formulations for parenteral administration may also be hyperosmotic relative to normal mammalian plasma, as described herein.

The terms buffer, buffer solution and buffered solution, when used with reference to hydrogen-ion concentration or pH, refer to the ability of a solute/solvent system, particularly an aqueous solution, to resist a change in pH with the addition of acid or alkali, or upon dilution with a solvent, or both. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydroxyl ion added does not exceed the capacity of the buffer system to neutralize it.

The buffer used in the practice of the present invention is selected from any of the following, for example, an acetate, phosphate, citrate, bicarbonate, glutamine, or glutamate buffer, with the most preferred buffer being a phosphate buffer.

Carriers or excipients can also be used to facilitate administration of the compositions and formulations of the invention. Examples of carriers and excipients include calcium carbonate, calcium phosphate, various sugars such as lactose, glucose, or sucrose, or types of starch, cellulose derivatives, gelatin, polyethylene glycols, and physiologically compatible solvents.

A stabilizer may be included in the formulations of the invention, but will generally not be needed. If included, however, a stabilizer useful in the practice of the invention is a carbohydrate or a polyhydric alcohol. The polyhydric alcohols include such compounds as sorbitol, mannitol, glycerol, xylitol, and polypropylene/ethylene glycol copolymer, as well as various polyethylene glycols (PEG) of molecular weight 200, 400, 1450, 3350, 4000, 6000, and 8000). The carbohydrates include, for example, mannose, ribose, trehalose, maltose, inositol, lactose, galactose, arabinose, or lactose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular agent will be effective in one formulation but not effective in another formulation.

A preservative is, in the common pharmaceutical sense, a substance that prevents or inhibits microbial growth and may be added to a pharmaceutical formulation for this purpose to avoid consequent spoilage of the formulation by microorganisms. While the amount of the preservative is not great, it may nevertheless affect the overall stability of the 2,2'-dithio-bis-ethane sulfonate. Preservatives include, for example, benzyl alcohol and ethyl alcohol.

While the preservative for use in the practice of the invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

A detailed description of each preservative is set forth in "*Remington's Pharmaceutical Sciences*" as well as *Pharmaceutical Dosage Forms: Parenteral Medications*, Vol. 1, Avis, et al. (1992). For these purposes, the 2,2'-dithio-bis-ethane sulfonate, a pharmaceutically-acceptable salt thereof, and/or an analog thereof, may be administered parenterally (including subcutaneous injections, intravenous, intramuscular, intradermal injection or infusion techniques) in dosage unit formulations containing conventional non-toxic pharmaceutically acceptable carriers, adjuvants, and vehicles.

If desired, the parenteral formulation may be thickened with a thickening agent such as a methylcellulose. The formulation may be prepared in an emulsified form, either water in oil or oil in water. Any of a wide variety of pharmaceutically-acceptable emulsifying agents may be employed including, for example, acacia powder, a non-ionic surfactant, or an ionic surfactant.

It may also be desirable to add suitable dispersing or suspending agents to the pharmaceutical formulation. These may include, for example, aqueous suspensions such as synthetic and natural gums, e.g., tragacanth, acacia, alginate, dextran, sodium carboxymethylcellulose, methylcellulose, polyvinylpyrrolidone, or gelatin.

It is possible that other ingredients may be present in the parenteral pharmaceutical formulation of the invention. Such additional ingredients may include wetting agents, oils (e.g., a vegetable oil such as sesame, peanut, or olive), analgesic agents, emulsifiers, antioxidants, bulking agents, tonicity modifiers, metal ions, oleaginous vehicles, proteins (e.g., human serum albumin, gelatin, or proteins) and a zwitterion (e.g., an amino acid such as betaine, taurine, arginine, glycine, lysine, or histidine). Such additional ingredients, of course, should not adversely affect the overall stability of the pharmaceutical formulation of the present invention.

Containers and kits are also a part of a composition and may be considered a component. Therefore, the selection of a container is based on a consideration of the composition of the container, as well as of the ingredients, and the treatment to which it will be subjected.

Regarding pharmaceutical formulations, see also, *Pharmaceutical Dosage Forms: Parenteral Medications, Vol. 1, 2nd ed.*, Avis et al., Eds., Marcel Dekker, New York, N.Y. (1992).

Suitable routes of parenteral administration include intramuscular, intravenous, subcutaneous, intraperitoneal, subdermal, intradermal, intraarticular, intrathecal, and the like. Mucosal delivery is also permissible. The dose and dosage regimen will depend upon the weight, health, disease type, and degree of disease severity affecting the subject.

In addition to the above means of achieving extended drug action, the rate and duration of delivery of 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)), may be controlled by, e.g., using mechanically controlled drug infusion pumps.

The invention in part provides infusion dose delivery formulations and devices, including but not limited to implantable infusion devices for delivery of compositions and formulations of the invention. Implantable infusion devices may employ inert material such as biodegradable polymers listed above or synthetic silicones, for example, cylastic, silicone rubber or other commercially-available polymers manufactured and approved for such uses. The polymer may be loaded with 2,2'-dithio-bis-ethane sulfonate and any excipients. Implantable infusion devices may also comprise a coating of, or a portion of, a medical device wherein the coating comprises the polymer loaded with 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)). Such an implantable infusion device may be prepared as disclosed in U.S. Pat. No. 6,309,380 by coating the device with an in vivo biocompatible and biodegradable or bioabsorbable or bioerodable liquid or gel solution containing a polymer with the solution comprising a desired dosage amount of 2,2'-dithio-bis-ethane sulfonate, a pharmaceutically-acceptable salt thereof, and/or an analog thereof, and any excipients. The solution is converted to a film adhering to the medical device thereby forming the implantable 2,2'-dithio-bis-ethane sulfonate-deliverable medical device.

An implantable infusion device may also be prepared by the in situ formation of 2,2'-dithio-bis-ethane sulfonate, a pharmaceutically-acceptable salt thereof, and/or an analog thereof, containing solid matrix as disclosed in U.S. Pat. No. 6,120,789, herein incorporated in its entirety. Implantable infusion devices may be passive or active. An active implantable infusion device may comprise a 2,2'-dithio-bis-ethane sulfonate reservoir, a means of allowing the 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)), to exit the reservoir, for example a permeable membrane, and a driving force to propel the 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)), from the reservoir. Such an active implantable infusion device may additionally be activated by an extrinsic signal, such as that disclosed in WO 02/45779, wherein the implantable infusion device comprises a system configured to deliver the 2,2'-dithio-bis-ethane sulfonate, a pharmaceutically-acceptable salt thereof, and/or an analog thereof, comprising an external activation unit operable by a user to request activation of the implantable infusion device, including a controller to reject such a request prior to the expiration of a lockout interval. Examples of an active implantable infusion device include implantable drug pumps.

Implantable drug pumps include, for example, miniature, computerized, programmable, refillable drug delivery systems with an attached catheter that inserts into a target organ system, usually the spinal cord or a vessel. See, Medtronic Inc. Publications: UC9603124EN NP-2687, 1997; UC199503941b EN NP-2347 182577-101, 2000; UC199801017a EN NP3273a 182600-101, 2000; UC200002512 EN NP4050, 2000; UC199900546bEN NP-3678EN, 2000. Medtronic, Inc., Minneapolis, Minn. (1997-2000). Many pumps have 2 ports: one into which drugs can be injected and the other that is connected directly to the catheter for bolus administration or analysis of fluid from the catheter. Implantable drug infusion pumps (e.g., SynchroMed EL and SynchroMed programmable pumps; Medtronic) are indicated for long-term intrathecal infusion of morphine sulfate for the treatment of chronic intractable pain; intravascular infusion of floxuridine for treatment of primary or metastatic cancer; intrathecal injection (baclofen injection) for severe spasticity; long-term epidural infusion of morphine sulfate for treatment of chronic intractable pain; long-term intravascular infusion of doxorubicin, cisplatin, or methotrexate for the treatment or metastatic cancer; and long-term intravenous infusion of clindamycin for the treatment of osteomyelitis. Such pumps may also be used for the long-term infusion of one or more compounds simultaneously, including, 2,2'-dithio-bis-ethane sulfonate, a pharmaceutically-acceptable salt thereof, (or prodrugs, analogs, conjugates, hydrates, solvates, or polymorphs, as well as stereoisomers (including diastereoisomers and enantiomers) and tautomers thereof)), in combination with one or more chemotherapeutic agents of choice, at a desired amount for a desired number of doses or steady state administration. One form of a typical implantable drug infusion pump (e.g., SynchroMed EL programmable pump; Medtronic) is titanium covered and roughly disk shaped, measures 85.2 mm in diameter and 22.86 mm in thickness, weighs 185 g, has a drug reservoir of 10 mL, and runs on a lithium thionyl-chloride battery with a 6- to 7-year life, depending on use. The downloadable memory contains programmed drug delivery parameters and calculated amount of drug remaining, which can be compared with actual amount of drug remaining to access accuracy of pump function, but actual pump function over time is not recorded. The pump is usually implanted in the right or left abdominal wall. Other pumps useful in the invention include, for example, Portable Disposable Infuser Pumps (PDIPs). Additionally, implantable infusion devices may employ liposome delivery systems, such as a small unilamellar vesicles, large unilamellar vesicles, and multilamellar vesicles can be formed from a variety of phospholipids, such as cholesterol, stearyl amine or phosphatidylcholines.

The invention also provides in part dose delivery formulations and devices formulated to enhance bioavailability of 2,2'-dithio-bis-ethane sulfonate, a pharmaceutically-acceptable salt thereof, prodrugs, analogs, conjugates, hydrates, solvates, and/or polymorphs, as well as stereoisomers (including diastereoisomers and enantiomers) and tautomers thereof. This may be in addition to or in combination with any of the formulations or devices described above.

An increase in bioavailability of 2,2'-dithio-bis-ethane sulfonate, may be achieved by complexation of 2,2'-dithio-bis-ethane sulfonate, a pharmaceutically-acceptable salt thereof, prodrugs, analogs, conjugates, hydrates, solvates, and/or polymorphs, as well as stereoisomers (including diastereoisomers and enantiomers) and tautomers thereof, with one or more bioavailability or absorption enhancing agents or in bioavailability or absorption enhancing formulations, including bile acids such as taurocholic acid.

The invention in part also provides for the formulation of 2,2'-dithio-bis-ethane sulfonate, a pharmaceutically-acceptable salt thereof, prodrugs, analogs, conjugates, hydrates, solvates, and/or polymorphs, as well as stereoisomers (including diastereoisomers and enantiomers) and tautomers thereof, in a microemulsion to enhance bioavailability. A microemulsion is a fluid and stable homogeneous solution composed of four major constituents, respectively, a hydrophilic phase, a lipophilic phase, at least one surfactant (SA) and at least one cosurfactant (CoSA). A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution. Examples of suitable surfactants include mono-, di- and triglycerides and polyethylene glycol (PEG) mono- and diesters. A cosurfactant, also sometimes known as "co-surface-active agent", is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

Any such dose may be administered by any of the routes or in any of the forms herein described. For example, a dose or doses could be given parenterally using a dosage form suitable for parenteral administration which may incorporate features or compositions described in respect of dosage forms delivered in a modified release, extended release, delayed release, slow release or repeat action oral dosage form.

A better understanding of the invention will be gained by reference to the following specific examples. The following examples are illustrative and are not intended to limit the invention or the claims in any way.

EXAMPLE 1

Preparation of Disodium 2,2'-dithio-bis-ethane Sulfonate Solution for Administration Sterile de-pyrogenated, disodium 2,2'-dithio-bis-ethane sulfonate that has been manufactured for parenteral administration to subjects, can be prepared for administration as follows.

All facilities and equipment are verified to be suitable for use in making pharmaceutical preparations (hereinafter "the preparation room"). After the facilities are verified to be suitably sterile, and has acceptable endotoxin, impurity, and contaminant levels, the solution from Example 1 is transferred to the preparation room. The preparation room is continuously monitored for airborne particles and viable flora as well as pressure differential compared to the pressure outside the preparation room. A heat belt is applied to a sterile vessel, of the appropriate size, containing the 2,2'-dithio-bis-ethane sulfonate composition (i.e., disodium 2,2'-dithio-bis-ethane sulfonate, and/or another pharmaceutically-acceptable salt, prodrugs, analogs, conjugates, hydrates, solvates, and/or polymorphs, as well as stereoisomers (including diastereoisomers and enantiomers) and tautomers thereof)) in solution form to warm the solution to between 35-40° C. After the solution has been allowed to sit at this temperature overnight, the solution is filtered through the 0.6 micron sterile pre-filter and then through the 0.2 micron sterile filter. When the solution has all passed through the filters, the filter is then bubble tested and flushed using a solution of 60% isopropyl alcohol and 40% water and the water bubble point of 11 psi should be reached. If the test fails, filtration must be repeated with new filters until a successful bubble test is obtained. A sample of the disodium 2,2'-dithio-bis-ethane sulfonate-containing solution is withdrawn and assayed for purity prior to proceeding to the filling step.

The solution is then transferred to a Flexicon® filling machine, which dispenses 6.0 g±0.1 g of solution into each sterile vial. A sterile stopper is then applied to each vial and finally a sterile seal is applied and crimped to each vial. A number of vials are removed for testing after filling and sealing. The number of vials filled is recorded and the vials transferred to a quarantine area for inspection. After the vials are inspected, a label having printed information regarding the contents, instructions for use, and/or safety information is affixed to each vial. The concentration of the disodium 2,2'-dithio-bis-ethane sulfonate, and/or other pharmaceutically-acceptable salt, and/or an analog thereof, contained in each vial marked on the label.

Calculation of the required amount of disodium 2,2'-dithio-bis-ethane sulfonate is made based upon the desired dose rate (e.g., grams or milligrams per $m^2$ per minute, without limitation) and that is considered appropriate by the treating physician for the patient's condition. For example, if a physician determines the need to treat the patient with disodium 2,2'-dithio-bis-ethane sulfonate in conjunction with the patient's chemotherapy to reduce, prevent, mitigate or delay toxicity, and has determined that the patient has a body surface area (i.e., as determined by an acceptable conventional methodology) of 1.7 $m^2$ and further decides that the desired dose rate of the disodium 2,2'-dithio-bis-ethane sulfonate solution to be administered is approximately about 695 mg/min, and a disodium 2,2'-dithio-bis-ethane sulfonate solution osmolarity of about 1,660 mOsm/L, to be administered over a period of 45 minutes total, the pharmacist would prepare the disodium 2,2'-dithio-bis-ethane sulfonate solution for administration as follows: (i) 695 mg/min×45 minutes=31,280 milligrams; (ii) next, the pharmacist would prepare a 20% (200 mg/mL) stock solution of disodium 2,2'-dithio-bis-ethane sulfonate in sufficient quantity for administration to the patient by calculation of 31,280 milligrams divided by 200 mg/mL=156.4 mL of the 20% disodium 2,2'-dithio-bis-ethane sulfonate solution. The 200 mg/mL stock solution is then diluted for various other desired concentrations.

When prepared for administration, the calculated amount of disodium 2,2'-dithio-bis-ethane sulfonate and/or another pharmaceutically-acceptable salt, prodrugs, analogs, conjugates, hydrates, solvates, and/or polymorphs, as well as stereoisomers (including diastereoisomers and enantiomers) and tautomers thereof, is either drawn from an appropriately manufactured 20% solution or immediately reconstituted in water, dextrose in water, physiological saline solution, dextrose and saline in water, or any other acceptable diluent that is approved for parenteral administration. The diluent is stored for use in parenteral injections in a suitable sterile, pyrogen-free, plastic or glass container that is designed for such administration.

EXAMPLE 2

Administration of a Disodium 2,2'-dithio-bis-ethane Sulfonate Solution

In the event it is further desired to administer a disodium 2,2'-dithio-bis-ethane sulfonate solution to the same or a different patient from the immediately preceding Example 1, that has a final osmolarity of about 830 mOsm/L and to administer said solution to the patient at the same dose rate, the adjustment in the osmolarity of the preparation of the disodium 2,2'-dithio-bis-ethane sulfonate solution and the administration of the same prepared solution may be as follows: (i) 156.4 mL of a 20% (200 mg/mL) disodium 2,2'-dithio-bis-ethane sulfonate solution would be added to 156.4 mL of water dextrose in water, physiological saline solution, dextrose and saline solution, or any other acceptable sterile diluent that is approved for use in parenteral administration, and placed in a suitable plastic or class container for said administration; (ii) the rate of the disodium 2,2'-dithio-bis-ethane sulfonate solution infusion would be increased by a factor of about 2 to ensure that the medication was administered within 45 minutes total time, if this was the total amount of time used in Example 1 to administer the disodium 2,2'-dithio-bis-ethane sulfonate solution infusion to the subject.

EXAMPLE 3

Administration of a Disodium 2,2'-dithio-bis-ethane Sulfonate Solution at a 100 mg/ml Concentration Over a 45 Minute Time Range Administration of an appropriately prepared solution of 2,2'-dithio-bis-ethane sulfonate, e.g., disodium 2,2'-dithio-bis-ethane sulfonate (and/or another pharmaceutically-acceptable salt, prodrugs, analogs, conjugates, hydrates, solvates, and/or polymorphs, as well as stereoisomers (including diastereoisomers and enantiomers) and tautomers thereof)), approximately 830 mOsm/L in final form, is carried out under a properly executed physician's order. The subject is administered intravenously a 100 mg/mL disodium 2,2'-dithio-bis-ethane sulfonate solution at a rate of about 7 mL/minute for 45 minutes total.

EXAMPLE 4

Administration of Disodium 2,2'-dithio-bis-ethane Sulfonate Solution with a Taxane Chemotherapeutic Agent Patients diagnosed with breast cancer received treatment with paclitaxel and disodium 2,2'-dithio-bis-ethane sulfonate; both medications were administered separately as a single daily intravenous infusion once every seven days. Paclitaxel was administered intravenously over a period of 1 hour at a dose of 80 mg/$m^2$. About 18.4 g/$m^2$ of disodium 2,2'-dithio-bis-ethane sulfonate was administered intravenously over 45 minutes, immediately following paclitaxel administration. The patients' body surface area (BSA) was determined based on the use of standard methods that are customarily used for such purposes, including standardized nomograms and calculations that utilize the individual height and weight data from each patient.

Disodium 2,2'-dithio-bis-ethane sulfonate was prepared as described in Example 1 and provided in glass bottles at a stock concentration of 200 mg/mL.

Calculating Dose: The dose and volume of disodium 2,2'-dithio-bis-ethane sulfonate for each patient was calculated with the following formula:

(18,400 mg/$m^2$×BSA in $m^2$) divided by 200 mg/mL=total dose in milliliters for each patient.

For example, a patient with a BSA of 1.76 m² would receive a total volume of 162 mL of stock solution calculated as follows:

(18,400 mg/m² divided by 200 mg/mL)×1.76 m²=92×1.76=162 mL

Calculating Concentration: The final concentration of the medication for each patient was calculated based on administration of a final disodium 2,2'-dithio-bis-ethane sulfonate concentration of 100 mg/mL.

Step 1: Calculation of Concentration Factor for Final Concentration to be Administered Starting concentration (mg/mL) divided by target concentration=X=concentration factor.

Step 2: Calculation of Volume of Final Concentration

Volume of starting concentration multiplied by X=final total volume.

For example, if the patient is to receive a dose of 162 mL of 200 mg/mL stock solution, the 162 mL of disodium 2,2'-dithio-bis-ethane sulfonate disodium would be added to an equal volume of sterile water for intravenous administration as follows:

STEP 1: 200 mg/mL divided by 100 mg/mL=2
STEP 2: 162 mL×2=324 mL (final total volume)

Calculating Rate: The rate of infusion was calculated based on a 45 minute infusion time.

Total Volume=mL/min divided by the total number of minutes.

For example, if the total volume is 324 mL, the rate would be about 7.2 or 7 mL/min. (i.e., 324 mL divided by 45 minutes equals 7.2 mL per minute).

Paclitaxel was diluted in 250 to 500 cc of 5% dextrose for Injection, USP or 0.9% sodium chloride for injection, USP. While 80 mg/m² is described above, other doses may also be administered. For example, paclitaxel may be administered from about 50 mg/m² to about 175 m², about 100 mg/m², including, for example, about 135 mg/m², about 150 mg/m² and about 175 mg/m². Additionally, alternative infusion times may include, for example, from about 1 hour to about 24 hours. Paclitaxel solutions may be prepared in accordance with the manufacturer's instructions on the label.

HER2 positive patients may have additionally received trastuzumab treatment. Trastuzumab was reconstituted prior to administration using exactly 20 mL of the bacteriostatic water supplied with the drug. The resulting stock solution contained 21 mg/mL of trastuzumab. Trastuzumab was further diluted before administration by adding the appropriate amount of drug to a polyvinyl chloride or polyethylene infusion bag containing 250 cm³ of 0.9% sodium chloride for injection, USP. The first dose of trastuzumab was 4 mg/kg administered intravenously over 90 minutes. All subsequent doses of trastuzumab were 2 mg/kg, administered over 30 minutes once weekly. Trastuzumab was administered following the completion of each dose of disodium 2,2'-dithio-bis-ethane sulfonate.

Optionally, patients may additionally receive pre-medications for paclitaxel and/or saline hydration. Pre-medications may include, for example, dexamethasone, diphenhydramine and H2 antihistamines including cimetidine, ranitidine or famotidine.

Dexamethasone may be administered according to the standard practice/regimen, however, the following taper is recommended to avoid cumulative dexamethasone toxicity in patients. 10 mg of dexamethasone for parenteral administration can be prepared in accordance with the manufacturer's label and administered intravenously 30 minutes prior to paclitaxel infusion during the first week, followed by 8 mg intravenously the second week, 6 mg intravenously the third week 3, 4 mg intravenously the fourth week, and 2 mg intravenously thereafter as long as paclitaxel treatment continues. If a patient receives a dexamethasone dose less than 10 mg and experiences any hypersensitivity reaction, the patient may receive the next higher dexamethasone dose, or other higher doses of dexamethasone if desired, prior to all further paclitaxel therapy.

If intravenous dexamethasone is not available, oral formulations of commercially available dexamethasone, at the same doses noted above, administered 4-6 hours prior to paclitaxel infusion may be used. Prednisone or prednisolone from commercial sources may be substituted for the above noted doses of dexamethasone at the following doses: dose dexamethasone (dose prednisone): 10 mg (60 mg), 8 mg (50 mg), 6 mg (40 mg), 4 mg (25 mg), or 2 mg (15 mg).

Diphenhydramine hydrochloride, from commercial sources, 50 mg may be administered intravenously 30 to 60 minutes prior to paclitaxel administration. Diphenhydramine should be prepared and administered to the patient in accordance with the manufacturer's instructions.

One of the following commercially available H2 antihistamine premedications may optionally be administered 30 to 60 minutes prior to paclitaxel administration: (i) i.v ranitidine hydrochloride 50 mg; (ii) i.v cimetidine hydrochloride 300 mg; or (iii) i.v. famotidine 20 mg. The H2 antihistamine that is administered to the patient should be prepared and administered in accordance with the manufacturer's instructions.

Saline hydration may include, for example administration of about 250 mL to about 1000 mL of 0.9% saline (sodium chloride) solution administered over about and hour to about 2 hours. Saline hydration steps can be administered, for example, prior to the administration of paclitaxel or after administration of disodium 2,2'-dithio-bis-ethane sulfonate.

EXAMPLE 5

Administration of Disodium 2,2'-dithio-bis-ethane Sulfonate Solution with a Taxane Chemotherapeutic Agent and a Platinum Chemotherapeutic Agent 2,2'-dithio-bis-ethane sulfonate, e.g., disodium 2,2'-dithio-bis-ethane sulfonate, may also be administered in combination with both a taxane chemotherapeutic agent and a platinum chemotherapeutic agent. This treatment regime is administered about once a week. Alternatively, the treatment regime is administered about once every two weeks, about once every two and a half weeks, or about once every three weeks.

Paclitaxel is administered intravenously over a period of 1 hour at a dose of 80 mg/m². Approximately 18 g/m² of disodium 2,2'-dithio-bis-ethane sulfonate is administered intravenously over 45 minutes, immediately following paclitaxel administration. Cisplatin, from commercial sources, is administered intravenously over a period of 1 hour, immediately following disodium 2,2'-dithio-bis-ethane sulfonate. Cisplatin may be administered at a dose from about 30 mg/m² to about 120 mg/m².

Disodium 2,2'-dithio-bis-ethane sulfonate is prepared as described in Example 1 and provided in glass bottles at a stock concentration of 200 mg/mL. Dose, concentration and infusion rate is calculated as described in Example 4, based on a dose of about 18.4 g/m², concentration of about 100 mg/mL and infusion time of about 45 minutes.

Optionally, patients also receive pre-medications for paclitaxel, pre-medications for cisplatin, and/or saline hydration.

Pre-medications may include, for example, antihistamines, steroids, antiemetics, and 5-HT3 antagonists. Antihistamines may include, without limitation, for example, diphenhydramine, clemastine, cimetidine, ranitidine and famotidine. Steroids may include, for example, corticosteroids, including hydrocortisone, dexamethasone, prednisolone and prednisone. Antiemetics may include, for example, prochloroperazine, metoclopramide, and dimenhydrinate. 5-HT3 antagonists may include, for example, ondansetron, dolasetron, and granisetron. Other pre-therapy drugs may include, for example, diazepam congeners, gabapentin and amitryptiline. Pre-therapy may be administered at least one day prior to chemotherapy, prior to each chemotherapy treatment, immediately prior to each chemotherapy treatment, concomitantly with or simultaneously during chemotherapy treatment, immediately subsequent to chemotherapy, subsequent to chemotherapy, and/or according to methods known within the art and in accordance with the patient's medical condition. Pre-medications may be administered according to the manufacture's instructions and as described in Example 4.

Saline hydration may include, for example administration of about 250 mL to about 1000 mL of 0.9% saline solution administered over about 1 hour to about 2 hours. Other forms of hydration, including hypertonic (e.g., 3% sodium chloride) or hypotonic (e.g., 0.45 sodium chloride or Dextrose 5% in Water or Ringer's lactate) solutions that are commercially available for parenteral administration may be used in lieu of, or in combination with, or in addition to saline hydration as dictated by the patient's medical condition. Hydration steps can be added prior to the administration of paclitaxel, after administration of disodium 2,2'-dithio-bis-ethane sulfonate, prior to the administration of cisplatin, and/or after the administration of cisplatin.

Discussion of Clinical Results

FIG. 1 and FIG. 2

Clinical study results support the administration of compounds such as disodium 2,2'-dithio-bis-ethane sulfonate, and/or another pharmaceutically-acceptable salt thereof, and/or an analog thereof, over a period of about 45 minutes and at a concentration of about 100 mg/mL, which resulted in an observed substantial decrease in the frequency of hypersensitivity Adverse Events over administration of the same compound over a period of 30 minutes at a concentration of 200 mg/mL. FIG. 1 illustrates a comparison of the number of hypersensitivity Adverse Events between groups of patients in whom 2,2'-dithio-bis-ethane sulfonate or a placebo was infused over (1) 30 minutes, (2) 30 minutes and 45 minutes, or (3) 45 minutes. In addition, the total number of hypersensitivity Adverse Events, the mean time to the first hypersensitivity Adverse Event, and a variety of the types of hypersensitivity Adverse Events were also shown. FIG. 1 shows the proportion of patients with at least one hypersensitivity Adverse Event was lowered from approximately 42% to approximately 30%. These results are based upon a double-blind, placebo-controlled study with a 1:1 randomization; which includes patients who received placebo, as well as all patients in cohorts treated with paclitaxel, which is known to produce Adverse Events (e.g., hypersensitivity reactions and more severe forms of allergic reactions including anaphylaxis). The overall expected value for paclitaxel alone is approximately 40-45% hypersensitivity reactions; however a reduction in the overall proportion of patients experiencing hypersensitivity Adverse Events by approximately 12% (i.e., approximately 42% to approximately 30%) was observed. This reduction in the proportion of patients experiencing hypersensitivity Adverse Events overall represents a reduction in the risk of an observed potentially serious and life-threatening Adverse Event by approximately 29% in the entire study population (i.e., both placebo and disodium 2,2'-dithio-bis-ethane sulfonate populations). As there is no additive or expected placebo induced-effect causing reported hypersensitivity reactions, there may be up to an approximate 57% reduction in such hypersensitivity events in the disodium 2,2'-dithio-bis-ethane sulfonate treatment population (e.g., approximately 42% observed overall, prior to the implementation of novel methods of administration to which the present invention relates, followed by approximately 30% observed incidence, after such implementation). In the aforementioned calculations, approximately 42% represents the incidence of Adverse Events observed or reported in the entire treated population who received paclitaxel plus either placebo or disodium 2,2'-dithio-bis-ethane sulfonate (i.e., 1:1 or approximately 50%, each) at 200 mg/mL over a total of 30 minutes; whereas approximately 30% represents the incidence of Adverse Events observed or reported in the entire treated population who received paclitaxel plus either placebo or disodium 2,2'-dithio-bis-ethane sulfonate (i.e., 1:1 or approximately 50% each) at 100 mg/mL over a total of 45 minutes.

FIG. 2 illustrates a comparison of the number of patients experiencing at least one drug-related Serious Adverse Effect (SAE) and those patients experiencing at least one drug-related grade 3 or greater Adverse Event (AE) between groups of patients wherein disodium 2,2'-dithio-bis-ethane sulfonate was infused over about 30 minutes, about 30 and about 45 minutes, or about 45 minutes. Drug concentrations administered were about 200 mg/mL infused over about 30 minutes, about 200 mg/mL and about 100 mg/mL infused over about 30 & about 45 minutes, respectively, and about 100 mg/mL infused over about 45 minutes. Results similar to that found in FIG. 1 were shown in FIG. 2, with an observed substantial decrease in the frequency of drug-related Serious Adverse Events with the administration of the disodium 2,2'-dithio-bis-ethane sulfonate over about 45 minutes and at a concentration of about 100 mg/mL when compared to an administration period of about 30 minutes at a concentration of about 200 mg/mL. The 45 minute administration of a compound with a concentration of about 100 mg/mL resulted in the proportion of patients experiencing at least one drug-related Serious Adverse Event (SAE) being lowered from approximately 7.6% to approximately 5.4%, an approximate 29% overall reduction. Moreover, the percentage of patients experiencing at least one drug-related grade 3 or greater Adverse Event was decreased from 16.4% (30 minutes, 200 mg/mL) to 8.6% (45 minutes, 100 mg/mL), an approximate 47% overall reduction. A full definition of Adverse Effects or Adverse Events is provided in paragraph [0070] and in part states, drug-related Adverse Events are rated from grade 1 to grade 5 and relate to the severity or intensity of the effect or event (grade 1 is mild, grade 2 is moderate, grade 3 is severe, grade 4 is life threatening, and grade 5 results in death).

EXAMPLE 6

Japanese Phase III NSCLC Paclitaxel+Cisplatin Clinical Trial

I. Summary of the Objectives and Methods of the Clinical Trial

Data was recently unblinded from a multicenter double-blind randomized placebo-controlled Phase III clinical trial of Tavocept™ (also known in the literature as BNP7787, 2,2'-dithio-bis-ethane sulfonate, and dimesna) conducted in Japan (herein the "Japan Phase III Clinical Trial") and involving patients with advanced non-small cell lung carcinoma (NSCLC) who received the chemotherapeutic drugs paclitaxel and cisplatin.

The primary objective of the Japan Phase III Clinical Trial was to show that the Formula (I) compound, Tavocept™, prevents and/or reduces peripheral neuropathy induced by paclitaxel+cisplatin combination therapy in patients with non-small cell lung carcinoma (NSCLC).

As described below, the primary clinical endpoint for the Japan Phase III Clinical Trial was specifically designed to demonstrate the existence of a new type of peripheral neuropathy called "intermittent neuropathy".

Patients admitted into the trial included those patients without previous treatment (excluding surgical treatment, administration of Picibanil into the serous membrane, irradiation of 30% or less hematopoietic bone, or oral chemotherapeutic agents within 3 months of entry in the trial).

The Japan Phase III Clinical Trial was conducted as a double-blind study because peripheral neuropathy is diagnosed based on subjective symptoms evaluated through clinical interviews, lab tests, and the like. Accordingly, evaluations by both physicians and patients are highly important. The present trial was designed to show that Tavocept™ prevents and/or reduces peripheral neuropathy induced by paclitaxel and cisplatin in NSCLC patients. A placebo was used as control since there is no established therapy or drug for preventing peripheral neuropathy. Because the severity of peripheral neuropathy is evaluated based on patients' reports (i.e., subjective symptoms), the Patient Neurotoxicity Questionnaire (PNQ©) (also known as the Peripheral Neuropathy Questionnaire) was used in primary evaluation. The CIPN-20 questionnaire and the National Cancer Institute-Common Toxicity Criteria (NCI-CTC) were used in secondary evaluation. The incidence and severity of adverse reactions, time to their onset, etc. and the like, were compared between patients treated with Tavocept™ and those given a placebo using the aforementioned methods.

In order to make these evaluations, Tavocept™ (approximately 14-22 $g/m^2$, most preferably approximately 18.4 $g/m^2$) or placebo (0.9% NaCl) was administered to non-small cell lung carcinoma (NSCLC) patients, including patients with adenocarcinoma, receiving chemotherapy with paclitaxel (approximately 160-190 $mg/m^2$, most preferably approximately 175 $mg/m^2$) and cisplatin (approximately 60-100 $mg/m^2$, most preferably approximately 80 $mg/m^2$), every 3 weeks (and repeated for a minimum of 2 cycles).

II. Summary of the Results of the Clinical Trial

The Japan Phase III Clinical Trial also provided a number of unexpected physiological results which have, heretofore, been unreported in any previous scientific or clinical studies. In brief, these unexpected and novel results include, but are not limited to, (i) the differentiation of chemotherapy-induced peripheral neuropathy into an entirely new class of peripheral neuropathy, called "intermittent" peripheral neuropathy; (ii) a medically important increase in survival for patients with NSCLC receiving Tavocept™ and chemotherapy; (iii) a medically important increase in survival time for patients with adenocarcinoma receiving Tavocept™ and chemotherapy; (iv) potentiation of the cytotoxic or apoptotic activities of chemotherapeutic agents in patients with non-small cell lung carcinoma and adenocarcinoma; (iii) increasing patient survival and/or delaying tumor progression while maintaining or improving the quality of life in patients with non-small cell lung carcinoma and adenocarcinoma; and (iv) the maintenance or stimulation of hematological function (e.g., an increase in hemoglobin, hematocrit, and erythrocyte levels), in patients with non-small cell lung carcinoma and adenocarcinoma.

In addition, there were concurrent observations in the clinical trial population of medically important reductions in chemotherapy-induced anemia, nausea/vomiting, fatigue, and kidney damage.

III. Peripheral Neuropathy

The term neuropathy is commonly utilized to refer to peripheral neuropathy, meaning a disease of the peripheral nerve or nerves. Peripheral neuropathy is the term for damage to nerves of the peripheral nervous system, which may result from a variety of causes. Peripheral neuropathies vary in their presentation and origin, and may affect either the nerve or the neuromuscular junction. The neuromuscular junction (NMJ) is the synapse or junction of the axon terminal of a motoneuron with the motor end plate (i.e., the highly-excitable region of muscle fiber plasma membrane responsible for initiation of nerve action potentials across the muscle's surface, ultimately causing the muscle to contract). In vertebrates, the signal passes through the neuromuscular junction via the neurotransmitter, acetylcholine.

The causes of peripheral neuropathy are broadly grouped as follows: (i) genetic diseases (e.g., Friedreich's ataxia, Charcot-Marie-Tooth syndrome, and the like); (ii) metabolic/endocrine (e.g., diabetes mellitus, chronic renal failure, porphyria, amyloidosis, liver failure, hypothyroidism, and the like); (iii) toxic causes (e.g., alcoholism, drugs (phenyloin, isoniazid, and especially chemotherapeutic drugs, including but not limited to, vincristine, cisplatin, taxanes, and the like), organic metals, heavy metals, and the like); (iv) inflammatory diseases (e.g., Guillain-Barré syndrome, systemic lupus erythematosus (SLE), leprosy, Sjögren's syndrome, and the like); (v) vitamin deficiencies (e.g., vitamin $B_{12}$, vitamin A, vitamin E, thiamin, and the like); and (vi) others causes (e.g., malignant disease, HIV, radiation, and chemotherapy). The major cause of drug-induced peripheral neuropathy is caused by chemotherapeutic agents.

It should be noted that many of the diseases of the peripheral nervous system may present similarly to muscle problems (myopathies), and so it is important to develop highly accurate and discriminating approaches for assessing sensory and motor disturbances in patients so that a physician may make an accurate diagnosis. Peripheral neuropathies may either be: (i) symmetrical and generalized or (ii) focal and multifocal, which is usually a good indicator of the cause of the peripheral nerve disease.

IV. Chemotherapy-Induced Peripheral Neuropathy (CIPN)

Aspects of the present invention are concerned with chemotherapy-induced peripheral neuropathy. Chemotherapy-induced peripheral neuropathy (CIPN) is a common and serious clinical problem that affects many patients receiving cancer treatment. This condition may pose diagnostic and management challenges for the clinician, particularly in patients with coexisting conditions or disorders that involve damage or dysfunction of the peripheral nervous system.

Many chemotherapeutic agents in use currently are associated with the induction of serious and dose-limiting CIPN that can adversely, and in some cases permanently, affect quality of life by interference with the patients' activities of daily living, and can also directly interfere with planned administration of chemotherapy—which may adversely affect the potential efficacy of treatment for the patient. The primary clinical objective in the evaluation of patients with potential CIPN is focused on determining the level of functional impairment involving activities of daily living. These clinical findings are used to make medical decisions to continue, modify, delay, or stop treatment. The drugs most commonly reported to cause CIPN include, but are not limited to, taxanes, platinum agents, vinca alkaloids, thalidomide, and bortezomib; however, there are many other agents that are associated with the development of CIPN.

The diagnosis of CIPN must be approached cautiously in patients with potential coexisting or prior conditions that involve or predispose to peripheral neuropathy, and in these patients, who may pose a diagnostic dilemma to the clinician, the neurologic evaluation should be directed at elucidation and differentiation of CIPN from other potential causes of peripheral neuropathy.

Currently there is no standard approved treatment for the prevention, mitigation, or management of CIPN. Consequently, the development of this toxicity can result in treatment delays, dose modifications and, in severe cases, cessation of a current form of treatment. Modification, delay, or cessation in a patient's therapy may partially or completely alleviate the adverse symptoms of CIPN, but such maneuvers may adversely affect treatment of the primary tumor, especially if the patient's malignancy is responding to treatment. The development and regulatory approval of safe and effective interventions to prevent or mitigate CIPN would be an important medical advancement for cancer patients.

An increasing amount of medical evidence strongly suggests that the incidence of CIPN is substantially underreported in clinical trials due to the subjective nature of CIPN, the lack of diagnostic standards, and important limitations in the available grading scales that are commonly used to assess CIPN. Underreporting may also be a consequence of the absence of an approved effective treatment for this complication of chemotherapy. The challenges in diagnosing and assessing the extent of patient functional impairment in a reliable and reproducible manner is a critical consideration for the clinician in practice for medical decision making as well as in designing and implementing controlled clinical trials involving prospective evaluation of neurotoxic chemotherapy or interventions aimed at the prevention or mitigation of CIPN.

The clinical manifestations of CIPN are subjective and predominantly manifest as purely or predominantly neurosensory symptoms; CIPN symptoms are most commonly reported in the form of a progressive distal symmetrically distributed symptoms of numbness, tingling, "pins and needles," burning, decreased or altered sensation, or increased sensitivity that may be painful in the feet and hands. The primary clinical objective is to determine the presence and severity of CIPN-associated symptoms that result in interference with activities of daily living, because such findings are critical for treatment decisions. Symptoms of motor weakness due to CIPN are less commonly reported, and when present, are observed in patients with more persistent and severe sensory findings.

Isolated motor weakness with the complete absence of sensory involvement due to CIPN has not been reported, and if such findings are observed in a patient, consideration should be given to other conditions that may produce pure motor weakness such as steroid myopathy, Eaton-Lambert syndrome, diabetic motor neuropathy, cachexia with decreased activity level, paraneoplastic motor neuropathy, and unmasked Charcot-Marie-Tooth (CMT) disease. In some patients it may be challenging to differentiate CIPN from the symmetrical, distal neurosensory manifestations that are associated with paraneoplastic sensory neuropathy, diabetic neuropathy, or toxic/metabolic neuropathies. Diagnostic elucidation of the underlying neuropathic disorder can be approached by careful evaluation of history and comparison to baseline findings and the time course of new neurosensory findings, recognizing that asymmetric, focal or proximal involvement, or complete loss of sensation are indicative of other etiologies. The most common coexisting condition that may pose a diagnostic dilemma is diabetic neuropathy, which can be asymmetric or symmetric, focal or diffuse, or manifest as mononeuritis multiplex and has many different clinical presentations and patterns. The most common form of diabetic neuropathy, the distal symmetric polyneuropathic form, has clinical symptoms and findings that may be similar to CIPN, which can be further elucidated by a careful evaluation.

The most commonly observed clinical findings that are diagnostic of CIPN are symmetric progressive onset of the following sensory symptoms and findings in a stocking-glove distribution: paresthesia, hyperesthesia, hypoesthesia, and dysesthesia, which more commonly appear earlier and with more pronounced symptoms in the toes and feet, with later involvement of the fingers and hands. Concurrent loss of deep tendon reflexes (loss of distal usually earlier than proximal) in the affected extremities with sensory deficits/dysfunction is an important diagnostic sign associated with greater neurosensory damage. Sensory findings, including diminished or absent proprioception, vibration, touch, two-point discrimination, sharp/dull discrimination, temperature, and touch/pain are typically diminished in the stocking-glove distribution in symptomatic patients. The onset of CIPN symptoms is usually gradually progressive, but some patients experience rapid onset of symptoms following administration of neurotoxic chemotherapy.

The most important and challenging diagnostic assessment in patients with CIPN is to determine the degree of functional impairment in the patient's activities of daily living because these findings alone determine the need for modification, interruption, or discontinuation of neurotoxic treatment. It is important to consider that the subjective nature of the patient symptoms and the degree of impairment by CIPN are analogous to patient symptoms of nausea, pain, and depression; the evaluation of the degree of severity and level of impairment of these requires patient cooperation. Accordingly, a clinical approach must be taken that enables reliable, convenient, and noninvasive elicitation and assessment of the diagnostic symptoms of CIPN for the day-to-day management of the patient, as well as to apply such methods in clinical trials of interventions for the prevention or mitigation of CIPN.

When sensory symptoms of CIPN are more severe, the patient commonly expresses symptoms of functional impairment of important activities of daily living such as being unable to walk, button clothing, drive, use a keyboard, or write. It may be challenging to elicit such information from some patients, and to address this consideration, there is an increased requirement for monitoring and following up on potential patient symptoms that may be due to CIPN by nursing and medical staff.

Many types of therapeutic interventions have been evaluated as potential neuroprotective agents for CIPN including amifostine, glutathione, glutamine/glutamate, calcium/magnesium infusions, neurotrophic factors, gabapentin, and carbamazepine. Some reasonable results have been reported from phase I and phase II trials with these interventions, but no definitive conclusions can be drawn regarding these approaches because all of these studies are underpowered for their endpoints or employ nonrandomized and/or uncontrolled trial designs. None of the empiric or investigational approaches to CIPN interventions has become a standard of care or has otherwise documented evidence of benefit in the prevention, mitigation, or treatment of CIPN. Additionally, many of these empiric therapies are associated with adverse effects that may limit their utility in patients, and it is currently unknown if there is any concurrent interference with the antitumor activity of chemotherapy by these approaches.

A. Pathogenesis and Pathophysiology of CIPN

The underlying pathophysiologic mechanisms for the development of CIPN have not been fully elucidated. A variety of proposed mechanism(s) are reported, and it is apparent that that a high degree of similarity exists in the pattern and spectrum of clinical manifestations of CIPN associated with the administration of different chemotherapeutic agents (e.g., vinca alkaloids, platinum agents, thalidomide, bortezomib, and taxanes). CIPN is generally thought to arise as a consequence of disruption of axoplasmic microtubule-mediated transport, distal axonal (Wallerian) degeneration, and direct damage to the sensory nerve cell bodies of the dorsal root ganglia (DRG). Demyelination (diffuse or segmental) secondary to chemotherapy is uncommonly reported (but occasionally observed with cisplatin, and reported for suramin, an investigational agent), and when observed, it is typically a secondary and isolated finding relative to the extent of axonal and DRG associated pathologic findings. It is important to note that CIPN is associated with administration of chemotherapeutic agents that cannot appreciably distribute across the blood-brain barrier (e.g., taxanes, platinum agents, vinca alkaloids, thalidomide, and bortezomib). Terminal axonal degeneration and axonal microtubule disruption are the most common pathologic processes observed in CIPN and have been reported in association with exposure to vinca alkaloids, platinum agents, taxanes, thalidomide, suramin, and others. Peripheral myelin degeneration (diffuse or segmental) has been reported in association with other agents such as perhexyline, hexanes, and amiodarone. Demyelination is far less commonly observed in CIPN, and myelin damage appears to be a secondary finding as compared to damage to the terminal axon or disruption of the axonal microtubulin architecture.

Taxanes and epothilones are known to induce abnormal tubulin polymerization by preventing tubulin depolymerization, whereas the vinca alkaloids depolymerize tubulin; all of these agents are known for their ability to disrupt cellular microtubulin structure and function. Monohydrated platinum has been demonstrated to directly disrupt the ability of tubulin to polymerize, which is most likely due to denaturation of tubulin by the formation of platinum-tubulin adducts involving the accessible cysteine residues on tubulin. These observations suggest that tubulin may be an essential target in the pathogenesis of CIPN. Tubulin, a ubiquitous cellular protein that is present in high cellular concentrations, plays an important role in numerous critical cellular processes and functions, including a critical role in normal physiologic functions of peripheral nerves. Because of the high degree of similarity in the clinical symptoms and signs of CIPN observed in association with administration of different chemical classes of neurotoxic chemotherapeutic drugs, a common underlying mechanism is suggested involving a potential toxic effect of taxanes, platinum agents, vinca alkaloids, and other neurotoxic chemotherapeutic agents that is mediated by drug interactions with neuronal tubulin.

One of the important anatomic targets for neurotoxic chemotherapeutic agents is the dorsal root ganglia (DRG) and the larger anatomic portions of afferent and efferent axons, which are located outside of the central nervous system (CNS). See, e.g., McKeage, M. J., et al., Nucleolar damage correlates with neurotoxicity induced by different platinum drugs. *Br J Cancer* 85:1219-1225 (2001). In contrast to the blood-brain barrier in the CNS, the DRG and peripheral axons lack an efficient neurovascular barrier, which allows the facile diffusion of large molecular weight compounds in the interstitium surrounding the DRG and along the axon filaments. In addition to capillary fenestrations in the vascular supply to the DRG and axons, there are open junctions between adjoining endothelial cells of the peripheral epineural blood vessels that allow proteins and drugs to pass readily from the blood into the extracellular space. This absence of a vascular barrier may play an important role in CIPN development, by allowing the relatively unimpeded exposure of the DRG and the peripheral axons to neurotoxic agents directly from the plasma. Protein-bound and unbound forms of drugs can gain direct access to the local epineurium and can readily diffuse along the nerve fascicles, a process that is facilitated by the hydrostatic capillary pressure gradient. The endoneural fascicles also lack lymphatics, which limit removal of toxic substances in the endoneural fluid, thereby allowing local accumulation of neurotoxic agents. Consistent with the foregoing considerations, autopsy and experimental studies have shown high concentrations of platinum in the DRG and high concentrations of taxanes in the peripheral axons as compared to significantly lower levels of these substances in the brain and spinal cord. See, e.g., Gill, J. S., and Windebank, A. J., Cisplatin-induced apoptosis in rat root ganglion neurons is associated with attempted entry into the cell cycle. *J. Clin. Invest.* 101:2842-2850 (1998).

Cisplatin and carboplatin exposure leads to direct damage of the DRG in animal models. See, e.g., Verdu E, Vilches J J, Rodriguez F J, et al. Physiological and immunohistochemical characterization of cisplatin-induced neuropathy in mice. *Muscle Nerve* 22:329-340 (1999). Cisplatin has been demonstrated to substantially interfere with and disrupt axonal microtubule assembly, vesicular axonal transport, and inhibit neurite outgrowth from neurons. See, e.g., Tulub, A. A., and Stefanov, V. E., Cisplatin stops tubulin assembly into microtubules. A new insight into the mechanism of antitumor activity of platinum complexes. *Int. J. Biol. Macromol.* 28:191-198 (2001). DRG neurons exposed to cisplatin in vitro demonstrated nuclear condensation, cell shrinkage, and fragmentation with maintenance of plasma membrane and intracellular organelle integrity. These studies demonstrate that cisplatin treated DRG neurons continue to enter the cell cycle before any detectable morphologic measure of cell death was observed. Cisplatin exposure appears to directly cause tubulin dysfunction and axonal degeneration, thereby interfering with the supply of nutrients to distal axons mediated by fast anterograde axoplasmic transport; tubulin and microtubulin function are critical for normal axoplasmic transport. In animal models, carboplatin induces a highly similar pattern of histopathologic (DRG and axonopathy with evidence of Wallerian degeneration) damage that appears indistinguishable from cisplatin induced toxicopathological findings, suggesting that cisplatin and carboplatin act upon a common intracellular target. See, e.g., Screnci, D., and McKeage, M. J., Platinum neurotoxicity: clinical profiles, experimental models and neuroprotective approaches. *J. Inorg. Biochem.* 77:105-110 (1999).

Taxane and vinca alkaloid exposure are also reported to disrupt microtubule structure and function in peripheral nerve axonal filaments (see, e.g., Cavaletti, G., et al., Distribution of paclitaxel within the nervous system of the rat after repeated intravenous administration. *Neurotoxicology* 21:389-393 (2001). A common feature of the underlying pathophysiology of CIPN for taxanes, cisplatin, carboplatin, and vinca alkaloids appears to be mediated in part by drug-induced damage or dysfunction of neuronal microtubules, and an increasing number of experimental findings point to the disruption or interference with of tubulin integrity and function by neurotoxic medications. Tubulin plays a critical role in normal anterograde (fast and slow) and retrograde axoplasmic transport of peripheral axons. The essential role of tubulin and the associated transport proteins (e.g., kinesin and actin) in the function of peripheral nerves pose challenges for mechanistic studies involving chemotherapeutic and neuroprotective agents, but there have been important advances in the development of mammalian peripheral nerve models that are aimed at further elucidation of the pathophysiologic mechanisms underlying CIPN induction. Clearly, there is an important need for the development of better translational preclinical models of CIPN.

The clinical diagnostic hallmark of dose-limiting CIPN is a distal symmetric sensory neuropathy, which may be accompanied by motor symptoms and signs in the same distribution as sensory findings in up to approximately half of the patients with CIPN. The clinically observed relative predominance of neurosensory symptoms with partial or complete sparing of peripheral motor function observed in CIPN has not yet been elucidated on a pathophysiologic or pharmacologic basis.

The following pathologic and pharmacologic mechanisms are postulated in an attempt to explain the predominance of the neurosensory relative to the neuromotor clinical presentation and manifestations of CIPN: (i) many of the commonly associated neurotoxic cancer chemotherapeutic agents associated with CIPN cannot cross the blood-brain barrier in appreciable concentrations, which largely excludes a centrally mediated neurotoxic process for the pathogenesis of CIPN; (ii) lower motor neurons nerve cell bodies are located in the anterior gray matter of the spinal cord; this location of neuron cell body distribution is relatively highly protected from neurotoxic drug exposure by the blood-brain barrier and the cord matter, leaving only the efferent portion of peripheral motor axons with exposure to neurotoxic chemotherapy; (iii) the nerve cell bodies and axons of the neurosensory neurons for touch, position, temperature, pressure, vibration, and tendon stretch receptors are located outside of the CNS in the DRG, and therefore the anatomic components of the peripheral sensory nerves are exposed to neurotoxic chemotherapy; (iv) axons of motor neurons are more heavily myelinated (type A-$\alpha$, the largest diameter fibers), which may also provide greater tolerance and sparing from drug-induced motor axon damage relative to smaller diameter myelinated (e.g., type A-$\beta$, $\gamma$ and $\delta$, and type B and C) sensory fibers; and (v) the observed relative sparing of neuromotor function could also be explained in part due to the presence of an intact upper motor neuron function (in situ stimulation), as well as a protected lower motor neuron cell body in the spinal gray matter.

It is important to consider that the CIPN does not manifest in a diffuse or dermatomal or focal distribution, and the characteristic length-dependent distal symptoms and longest anatomical peripheral nerve fibers. This distribution of damage/dysfunction suggests that the peripheral neurons with the greatest length as well as containing the largest amounts of tubulin, kinesin, and actin and other neural proteins that may be targets of toxicity are involved in the observed increase in susceptibility to the acute or cumulative neurotoxicity that are observed in patients with CIPN.

B. Clinical Diagnostic Features of CIPN

The onset of CIPN is more typically gradually progressive, but some patients have rapid onset or a sporadic (i.e., intermittent) pattern following administration of neurotoxic chemotherapy. The diagnosis of CIPN must be distinguished from other etiologies that may be confounding, such as paraneoplastic sensory neuropathy, diabetic neuropathy, or toxic/metabolic neuropathies. This diagnostic differentiation is based on history and comparison to baseline findings and the time course of new neurosensory findings, recognizing that asymmetric, focal or proximal involvement, or complete loss of sensation are indicative of other etiologies.

Essential diagnostic features of CIPN include (i) distal length-dependent involvement of the longest peripheral nerve segments (e.g., glove and stocking distribution); (ii) symmetrical, distribution of involvement-absence of either dermatomal or focal isolated peripheral nerve involvement (e.g., median or common peroneal nerve); (iii) temporal onset following neurotoxic chemotherapy administration with progressive symptoms/signs that may temporarily resolve or progress (axonopathy), or rapid onset of symptoms/signs shortly following chemotherapy administration (neuronopathy); (iv) signs and symptoms of peripheral neurosensory dysfunction, which may include paresthesia, dysesthesia, hypoesthesia, and pain; and (v) relative sparing of motor function with mild to moderate motor weakness that may be accompanied by myoatrophy in the same clinical distribution as sensory finding. An essential diagnostic feature of CIPN is the relative disproportionate degree of sensory symptoms reported clinical findings in relationship to motor symptoms and findings. The Applicant speculates based upon clinical impression and limited unpublished data that CIPN may also exhibit age dependance. CIPN may manifest early and more frequently in older patients. This hypothesis may be supported by several future randomized studies.

Clinical evaluation of patients with suspected CIPN is focused on the location and distribution of symptoms and signs, noting the temporal relationship to chemotherapy administration, and the character and severity of sensory symptoms with particular attention to interference or disruption of activities of daily living. Localized areflexia, which involves distal reflexes first and may progress to proximal involvement, if present, is a helpful diagnostic sign of more advanced forms of CIPN. Complete loss of distal deep tendon reflexes (e.g., Achilles or brachioradialis) of the affected extremities can be confirmed by performing reinforcement maneuvers. The proper use of reinforcement reflex testing is a more reliable means to determine true absence of deep tendon reflexes in patients. Clinical examination of symptomatic patients commonly demonstrates impairment of light touch, two-point discrimination, sharp/dull, proprioception, temperature, and vibration in a symmetric stocking-glove pattern. Patients with CIPN may demonstrate an abnormal Romberg's test and may have some degree of ataxia. Romberg's test can be abnormal due to many etiologies, including labyrinthine disorders, cerebellar disorders as well as dorsal column dysfunction or damage, and motor weakness. Ataxia is nonspecific for CIPN; however, if present suggests a more severe degree of involvement.

Before administration of neurotoxic chemotherapy, identification of prior or coexisting medical conditions (e.g., diabetes, HIV, alcoholism, paraneoplastic neuropathy) or neurotoxic medications, nutritional deficiency (e.g., $B_{12}$, pyridoxine, or α-tocopherol deficiencies), or pyridoxine intoxication, a past history of neuropathy, prior neurotoxic and any family history of hereditary neuropathies should be obtained. Commonly used medications including, but not limited to, metronidazole, misonidazole, colchicine, sulfasalazine, nitrofurantoin, tacrolimus, nucleoside analogs (zalcitabine, didanosine, stavudine, and lamivudine), hydralazine, phenyloin, isoniazid, perhexyline, and disulfuram are associated with the development of peripheral neuropathy, and the clinician must consider that prior or continued use of such medications may complicate the management of patients who are subsequently treated with neurotoxic chemotherapy.

A baseline clinical neurologic evaluation performed before administration of neurotoxic chemotherapy is important for patient management. In patients with preexisting neurologic conditions, clinical evaluation by a neurologist may be invaluable in the future management of these patients.

Before the administration of potentially neurotoxic chemotherapy, particularly vincristine, it is important to evaluate patients for CMT disease, which is usually an autosomal dominant motor and sensory disorder affecting nerves and muscles of the distal extremities. Patients with Type I CMT disease present in middle childhood with footdrop and slowly progressive distal muscle atrophy, producing "stork legs" due to peroneal atrophy; wasting of the intrinsic muscles of the hands has a later onset. Patients with CMT may have other neurodegenerative diseases (e.g., Friedrich's ataxia) as well. Clinically, patients with CMT disease will demonstrate a stocking-glove distribution of impaired vibration, pain, and temperature sensation with absent deep tendon reflexes. Such patients usually have nearly or completely normal nerve conduction velocities but will demonstrate low amplitude evoked potentials when tested. Neural histopathology in symptomatic patients usually demonstrates Wallerian degeneration of distal axons. Patients with CMT have increased sensitivity to neurotoxic chemotherapy, particularly vincristine, which must be avoided because these patients are at risk for development of severe and potentially irreversible neuropathy that can mimic Guillain-Barr'e syndrome.

C. Diagnostic Classification of CIPN

CIPN can be diagnostically classified as a distal axonopathy, less commonly as a neuronopathy, and may simultaneously manifest with both forms in some patients. Distal axonopathy involves disruption of peripheral nerve function affecting axonal function and transport, resulting in retrograde Wallerian type of degeneration of terminal sensory axons and to a lesser extent, motor axons. Neuronopathy is the result of direct toxic damage to DRG neuronal cell bodies; with serious damage or death of DRG cell bodies, the attached axons undergo anterograde degeneration, resulting in destruction of axons, many or all of which may fail to regenerate. See, e.g., Chaudhry. V., et al., Toxic neuropathy in patients with pre-existing neuropathy. *Neurology* 60:337-340 (2003).

CIPN neuronopathy is characterized by rapid onset of symmetric distal sensory neuropathy following administration of neurotoxic chemotherapy. There is simultaneous involvement of upper and lower extremities, as well as cranial nerves, and there is the rapid and complete loss of all deep tendon reflexes. Id.

Patient symptoms and findings occur very quickly (within hours to several days) usually after one or two treatments, and are more common with higher doses of neurotoxic chemotherapy. The sensory symptoms and findings of CIPN neuronopathy have a rapid onset and are persistent; there is a distinct absence of slowly progressive or waxing and waning symptoms and signs in patients with this form of CIPN. The patient's sensory symptoms are usually permanent, presumably due to the loss of nerve cell bodies in the DRG and anterograde Wallerian degeneration of the peripheral axons. Motor weakness and atrophy may be observed in affected extremities, but CIPN neuronopathy usually spares motor function relative to the degree of sensory symptoms and findings observed.

Administration of taxanes or platinum therapy have been associated with the development of neuronopathy, particularly with higher doses or when combination neurotoxic therapy is administered. See, e.g., Openshaw, H., et al., Neurophysiological study of peripheral neuropathy after high-dose paclitaxel. *Clin. Cancer Res.* 10:461-467 (2004).

Distal axonopathy is the most common clinical presentation of CIPN, and is most commonly described as progressive or waxing and waning in onset usually becoming manifest after multiple cycles of treatment. The axonopathy form of CIPN is characterized by a distal symmetric predominantly sensory neuropathy with paresthesia, dysesthesia, burning, pain, or numbness that more commonly initially involves the lower extremities, and may later involve the upper extremities in a stocking-glove distribution. Axonopathy neurosensory symptoms can progress with additional treatment, and in more severe cases, it is accompanied by progressive loss of distal deep tendon reflexes and ataxia. The patient's symptoms and interference with function can worsen and improve between treatments, but most commonly progress with additional treatment, eventually become persistent between cycles or the passage of time, in some cases progressing even after treatment is delayed or discontinued. The waxing and waning of neurosensory symptoms may be related to partial or temporary recovery from damage or disruption of microtubule function and/or Wallerian regeneration of terminal axons.

Motor weakness and atrophy in the affected extremities is variable and is usually mild or moderate in approximately half of the affected patients. Distal weakness may be detected in patients with CIPN axonopathy and may be accompanied by signs of symmetric myoatrophy, which can be a helpful diagnostic finding. Relatively common observations in patients with CIPN axonopathy-associated motor weakness include (i) motor symptoms that are not perceived or reported by the patient, but are observed on clinical examination; (ii) distal weakness or decreased muscle mass, usually mild to moderate and not typically interfering with functional activity; (iii) sensory symptoms and abnormalities and resulting interference with functional activities reported by the patient that are usually far more disturbing to them than the motor symptoms; and (iv) it is not uncommon for patients to express increasing concerns regarding progressive exacerbation or the persistence of their symptoms and impairment. The progressive crescendo pattern and severity of symptoms and potential interference with function associated with CIPN axonopathy may worsen with the continuation of treatment and may progress after complete cessation of treatment with agents such as cisplatin, carboplatin, oxaliplatin, thalidomide, or taxanes.

Pure motor neuropathy, unaccompanied by any sensory symptoms, deficits, or dysfunction, has not been reported for CIPN. Isolated motor symptoms and signs in a patient with cancer suggests other etiologies, including paraneoplastic motor neuropathy or myopathy, steroid-induced (proximal involvement is more common) or drug-induced myopathy, myasthenia gravis, or Eaton-Lambert syndrome. It may be difficult to determine if there is motor involvement with CIPN due to the presence of the coexisting medical conditions, which include many possible etiologies, and most commonly by the presence of generalized weakness that is exacerbated by poor nutritional status, toxic neuropathy, cachexia, or debilitation. The insidious onset of symmetric, distal sensory impairment/loss with proximal muscle weakness (especially in the hips and thighs), characterized by an observed increase in strength with repeated contractions (facilitation), that can be accompanied by autonomic disturbances (e.g., sweating, tachycardia) and occasional ocular involvement, are key diagnostic features of the Eaton-Lambert myasthenic syndrome. The Eaton-Lambert myasthenic syndrome is most commonly observed in patients with small-cell lung cancer, and has been reported in patients with non-small cell lung cancer, lymphoma, malignant thymoma, and carcinomas of the breast, stomach, colon, prostate, bladder, kidney, or gall bladder. In patients treated with taxanes and/or vinca alkaloids there may be myalgias that are severe and persistent enough to result in muscular atrophy, which may coexist with CIPN in patients.

Distal axonopathy is the most commonly reported clinical manifestation of CIPN for all classes of neurotoxic chemotherapy, including platinum, vinca, and taxane therapy. Clinical features of thalidomide and bortezomib CIPN most commonly manifest as axonopathy. If the extent of axonal damage is limited, the terminal axons can regenerate, thereby manifesting as partial or complete symptom recovery between treatment cycles, or following treatment delays or cessation.

D. Clinical Problems Associated with CIPN

Many commonly used chemotherapeutic agents are associated with dose-limiting CIPN including, but not limited to, taxanes (e.g., docetaxel and all formulations/derivatives of paclitaxel), platinum agents (e.g., cisplatin, carboplatin, and oxaliplatin), and vinca alkaloids (e.g., vincristine, and less commonly vinblastine, vindesine, and vinorelbine). See, e.g., Screnci, D., and McKeage, M. J., Platinum neurotoxicity: clinical profiles, experimental models and neuroprotective approaches. *J. Inorg. Biochem.* 77:105-110 (1999). More recently, the use of thalidomide and bortezomib has been reported to have an association with the development of dose- and treatment-limiting CIPN.

The incidence and prevalence of CIPN in patients undergoing chemotherapy as well as the proportion of patients with persistence or resolution of CIPN following treatment are not known, but the occurrence of CIPN is widely reported in various controlled and uncontrolled studies in association with the administration of various chemotherapeutic agents. See, e.g., Rosell, R., et al., Phase III randomised trial comparing paclitaxel/carboplatin with paclitaxel/cisplatin in patients with advanced non-small-cell lung cancer: a cooperative multinational trial. *Ann. Oncol.* 13:1539-1549 (2002). In addition, the proportion of patients who experience treatment delays or discontinuation secondary to CIPN is rarely reported in clinical studies, and there is a lack of well-controlled clinical data regarding the time to onset, duration, and resolution or persistence of CIPN in the medical literature.

Most of the earlier clinical studies for drugs such as cisplatin, carboplatin, oxaliplatin, paclitaxel (including the paclitaxel-containing formulations Abraxane, Tocosol and Xyotax), epothilones, and docetaxel report substantially lower incidences of more severe CIPN, in contrast to later studies involving larger patient populations. This apparent underreporting of CIPN in earlier stages of drug development may be due in part to the absence of sufficiently sensitive and reliable diagnostic instruments for the assessment and reporting of CIPN. Another contributing factor may include the underassessment and the high degree of variability of the reported incidence and severity of CIPN associated with the currently available diagnostic and reporting methods used in these trials. In addition, comparison of CIPN incidence rates and outcomes becomes difficult across studies when different assessment methods are employed.

The importance of CIPN has increased with the advent and increased utilization of newer neurotoxic medicines, and supportive care interventions to prevent or mitigate toxicities of other organs (e.g., neutropenia), along with the increased utilization of dose-dense and weekly treatment regimens and drug combinations involving more than one neurotoxic compound. The incidence and severity of CIPN depends on the dose, schedule, and duration of neurotoxic agent(s) administered to the patient, as well as any coexisting or preexisting conditions that may predispose the patient to an increased incidence of more severe forms of CIPN. The use of multimodal neurotoxic therapy involving the combination of agents such as taxane and platinum agents, which has resulted in improved patient survival, has also resulted in a greater reported incidence of CIPN. In addition, the use of weekly taxane therapy in patients with metastatic breast cancer was recently reported to result in a significantly higher objective tumor response rate, time-to-progression, and overall survival as compared with the standard every 3-week treatment regimen. See, e.g., Seidman, A. D., et al., CALGB 9840: Phase III study of weekly paclitaxel via 1-hour (h) infusion versus standard 3 h infusion every third week in the treatment of metastatic breast cancer, with trastuzumab for HER2 positive MBC and randomized for T in HER2 normal MBC [Abstract #512]. 22:6s *Proc. Am. Soc. Clin. Oncol.* (2004).

The use of dose-dense and weekly taxane regimens is accompanied by an increased incidence and prevalence of CIPN, which further underscores the need for diagnostic methods for management and reporting as well as a safe and effective intervention.

IV. Neurotoxicity of Paclitaxel and Cisplatin

Peripheral neuropathy has been found to be a dose-limiting toxicity (DLT) in various clinical studies (see, e.g., Chaudry, V., et. al., Peripheral neuropathy from taxol and cisplatin combination chemotherapy: clinical and electrophysical studies. *Ann. Neurol.* 35:304-311 (1994); Von Pawel, J., et. al., Phase II study of paclitaxel and cisplatin in patients with non-small cell lung cancer. *Semin. Oncol.* 23:47-50 (1996)), and effective chemotherapy had to be discontinued because of neuropathy.

Paclitaxel-induced neuropathy is related to the one-time or cumulative dose of paclitaxel and co-administration of other drugs with neurotoxic effects such as cisplatin. Paclitaxel-induced neuropathy may include: (i) sensory neuropathy; (ii) motor neuropathy; (iii) autonomic neuropathy; (iv) myopathy; and (v) central neuropathy. See, e.g., Rowinsky, E. K. and Donehower, R. C., Paclitaxel (Taxol). *N. Engl. J. Med.* 332: 1004-1014 (1995). Among symptoms of paclitaxel-induced neuropathy, sensory (peripheral) nervous disorders such as numbness which shows a glove-stocking type distribution, pain, and causalgia are most commonly reported. These symptoms usually occur at an early stage after treatment (i.e., 24-72 hours after treatment) and worsen as treatment is repeated, frequently with concomitant motor nerve disorders such as weakness occurring at the same time. Id. In addition, autonomic nervous disorders such as paralytic ileus, orthostatic hypotension, and cardiac disorders (such as arrythmia), as well as myalgia, may also occur. In general, myalgia occurs 2-3 days after administration and disappears 5 or 6 days later.

Risk factors for neuropathy include high doses, co-administration with other drugs with neurotoxic effects, and a history of diabetes or alcohol abuse.

Cisplatin-induced neuropathy is related with the dose of cisplatin, and it usually occurs when the cumulative dose of cisplatin exceeds 300 mg/m². The treatment period and regimen are also reported to be related to the onset of cisplatin-induced neuropathy. See, e.g., Mollman, J. E., Cisplatin neurotoxicity. *N. Engl. J. Med.* 322(2):126-127 (1990). Usually, it occurs after long-term treatment (4-7 months), but it may also occur after the initial treatment. Signs and symptoms of neuropathy generally occur during the treatment period, but they may also occur several weeks after completion of the treatment. Worsening may also be seen after completion of the treatment. Cisplatin-induced neuropathy is reported as sensory peripheral neuropathy and can be associated with symptoms such as motor disorders (e.g., reduced reflex or loss of reflex and weakness), Lhermitte syndrome, autonomic neuropathy, major or focal seizure, encephalopathy, transient cortical blindness, retrobulbar optic neuritis, and retinal injury. See, e.g., DeVita, V, et al., *Cancer Principles & Practice of Oncology, 6th Ed.* (2001). The incidence of peripheral neuropathy due to paclitaxel and cisplatin co-administration therapy is reported to range between 39% and 71%, with incidence of 12.5-42.1% for Grade 2 or more severe peripheral neuropathy. See, e.g., Sakai, H., et al., A phase II study of Paclitaxel plus Cisplatin for advanced non-small-cell lung cancer in Japanese patients. *Cancer Chemother. Phamacol.* 48:499-503 (2001).

Concurrent administration of cisplatin and paclitaxel has demonstrated an enhanced potential for neurotoxicity (e.g., peripheral neuropathy) and is related to the drug doses and schedules utilized. At the commonly used dosages of these two drugs, more than 50% of patients develop peripheral neuropathy, and this side effect is frequently dose limiting. See, e.g., Berger, T., et al., Neurological monitoring of neurotoxicity induced by paclitaxel/cisplatin chemotherapy. *Eur. J. Cancer* 33:1303-1309 (1997).

A. Inhibitory Effects of a Formula (I) Compound in a Paclitaxel-Induced Neuropathy Model Paclitaxel (6 mg/kg) was intravenously administered 5-times every other day to rats, and the effect of Formula (I) compound, Tavocept™ (dimesna; disodium 2,2'-dithio-bis-ethane sulfonate), on paclitaxel-induced thermoparesthesia (i.e., a lack of reaction to hot or, rarely, cold objects placed on the skin) was evaluated. Paclitaxel-induced thermoparesthesia was inhibited 27.5-59.2% (significant inhibition) by intravenously administering 1,000 mg/kg of Tavocept™ immediately after administration of paclitaxel. The maximum inhibition rate achieved by 1,000 and 2,000 mg/kg of Tavocept™ was 41.7% and 41.5%, respectively, and there were no significant differences between the two dose groups.

Effects of Tavocept™ on thermoparesthesia caused by i.p. injection of 12 mg/kg of paclitaxel once a week for 5 weeks were evaluated. Thermoparesthesia caused by paclitaxel was significantly inhibited by administering 2,000 mg/kg of Tavocept™ by i.v. injection immediately after administration of paclitaxel. Inhibition rates of 19.2-34.1% were achieved.

Paclitaxel (6 mg/kg) was intravenously administered to rats 5-times every other day, and the effect of Tavocept™ on decreases in the nerve conduction velocity (NCV) induced by paclitaxel was evaluated. Paclitaxel-induced decreases in NCV were inhibited by 92.2% when 1,000 mg/kg of Tavocept™ was intravenously administered immediately after administration of paclitaxel.

Effects of Tavocept™ on histopathological abnormalities of the sciatic and tibial nerves caused by i.v. injection of 30 mg/kg of paclitaxel every other day (3 doses) were then evaluated. Increases in the incidence of histopathological abnormalities of the sciatic and tibial nerves were inhibited by intravenously administering 2,000 mg/kg of Tavocept™ immediately after administration of paclitaxel.

Inhibitory Effects of a Formula (I) Compound on a Cisplatin-Induced Neuropathy Model Effects of the Formula (I) compound, Tavocept™ (dimesna; disodium 2,2'-dithio-bis-ethane sulfonate), on decreases in nerve conduction velocity (NCV) induced by cisplatin (2 mg/kg) administered by i.p. injection twice a week for 6 consecutive weeks were evaluated in rats. Decreases in NCV by cisplatin were significantly inhibited by Tavocept™ when it was intravenously administered at 1,000 mg/kg immediately before administration of cisplatin. Inhibition rates of 53.6% and 64.7% were obtained, respectively, for decreases in NCV observed 5 and 6 weeks after starting cisplatin administration.

V. Postulated Mechanism of Action of Tavocept™ on Neuropathy

A. Mechanism of Action by which Tavocept™ Inhibits Paclitaxel-Induced Neuropathy Paclitaxel is a useful anti-malignant tumor agent effective for not only breast cancer but also other cancers including ovarian and lung cancer. However, neuropathy such as numbness of the hands and feet is one of its dose-limiting adverse effects. Tavocept™ has shown inhibitory effects on paclitaxel-induced neuropathy models.

Paclitaxel-induced neuropathy is thought to be attributable to the hyperplasia of microtubules (see, e.g., Monitti, A. M., et al., Resistance to antimitotic drugs in Chinese hamster ovary cells correlates with changes in the level of polymerized tubulin. *J. Biol. Chem.* 266:3987-3994 (1991)) and the loss of their dynamic instability (see, e.g., Jordan, M. A., et al., Mechanism of mitotic block and inhibition of cell proliferation by taxol at low concentrations. *Proc. Nail. Acad. Sci. USA.* 90:9552-9556 (1993)) induced by paclitaxel penetrating the nerve cell axons. Tavocept™ taken up by cells is thought to inhibit paclitaxel-induced neuropathy by preventing paclitaxel from binding to microtubules. Results from an in vitro study have demonstrated that Tavocept™ inhibits tubulin polymerization induced by paclitaxel (6 µM) at 6 mM. See, e.g., Hausheer, F., et al., BNP7787: A novel chemoprotecting agent for platinum and taxane toxicity. *Proc. Am. Assoc. Cancer Res.* 41:769 (2000). Additionally, the findings from another in vitro study showed that paclitaxel does not directly react with Tavocept™ or mesna (see, e.g., Cavalletti, E., et al., Oral and intravenous BNP7787 protects against paclitaxel-mediated neurotoxicity in Wistar rats. *Proc. Am. Assoc. Cancer Res.* 40:398 (1999)). Thus, the inhibition of paclitaxel-induced microtubular hyperplasia by Tavocepe™ is not considered to be attributable to its binding with paclitaxel; rather it is thought to decrease binding of paclitaxel to microtubules as a result of its effect on microtubules or tubulin, one of their constituent proteins.

B. Mechanism of Action by which Tavocept™ Inhibits Cisplatin-Induced Neuropathy

Cisplatin is effective for treating various types of cancer including ovarian and lung cancer, but various adverse reactions such as nephropathy and neuropathy limit its clinical use. Tavocept™ has been shown to exert inhibitory effects on various cisplatin-induced neuropathy models.

Cisplatin exerts its cytotoxic effects by binding with adenine and guanine of DNA chains in cell, but its activity is attributable to its monoaquo or monohydroxy body obtained as a result of its transformation in cells, and not cisplatin itself. See, e.g., Reed., E., et al., Platinum analogues. *Cancer*

*Chemotherapy and Biotherapy* Lippincott-Raven, Philadelphia, New York, pp. 357-378 (1996). After intravenous administration, Tavocept™ is rapidly taken up in the kidney and metabolized into mesna in cells using intracellular glutathione as a cofactor. Because mesna has free SH-groups in its molecule, it binds with monohydroxy and monoaquo bodies of cisplatin in cells thereby preventing cytotoxic effects of these cisplatin metabolites, or it inhibits cisplatin-induced neuropathy by maintaining normal tubulin polymerization. See, e.g., Hausheer, F., et al., BNP7787: A novel chemoprotecting agent for platinum and taxane toxicity. *Proc. Am. Assoc. Cancer Res.* 41:769 (2000).

VI. Novel Intermittent or Sporadic Form of Chemotherapy-Induced Neuropathy

Aspects of the present invention relate to a novel type of peripheral neuropathy called "intermittent" or "sporadic" peripheral neuropathy. It should be noted that, prior to the present invention, the medical community has considered chemotherapy-induced peripheral neuropathy to consist only of the cumulative or persistent variety (defined below). The heretofore unreported, intermittent or sporadic form of chemotherapy-induced peripheral neuropathy is defined by its non-persistent presence followed by absence, which may be followed by a variable and intermittent recrudescent occurrence of symptoms and or functional impairment due to neurotoxicity, that are temporally associated with the administration of neurotoxic chemotherapy. Intermittent chemotherapy-induced peripheral neuropathy is characterized by the unpredictable, randomly episodic presence and disappearance of neuropathy symptoms and signs. Persistent or cumulative neuropathy is distinguished from intermittent or sporadic neuropathy by the persistent and continuous nature of neurotoxic symptoms and/or functional impairment due to neurotoxicity that are temporally observed with the administration of chemotherapy, and further bear a relationship to the total dose and cumulative amount of neurotoxic chemotherapy administered to the patient.

The Primary Endpoint of the Japan Phase III Clinical Trial described in the present invention was specifically designed to test the hypothesis of whether chemotherapy-induced intermittent peripheral neuropathy would occur. The utilization of physical examination, laboratory tests, and highly detailed patient evaluation, especially utilizing the Patient Neurotoxicity Questionnaire (PNQ©), also known as the Peripheral Neuropathy Questionnaire, was responsible for the identification and characterization of this novel intermittent form of chemotherapy-induced peripheral neuropathy. The results illustrated in FIG. 3 indicate that intermittent peripheral neuropathy was specifically identified and measured in the Japan Phase III Clinical Trial. Specifically, in FIG. 3, the numerical value of 0.1565 in the tabular row designated "Drug" under the tabular column designated "P-Value" demonstrates that there is only a 15.65% probability that the reduction in intermittent and cumulative peripheral neuropathy observed for Tavocept™ (also known as BNP7787) in the Japan Phase III Clinical Trial is due to random chance alone. Additionally, the results illustrated in FIG. 4 and FIG. 5 also support the finding that the Formula (I) compound, Tavocept™, can mitigate and/or prevent intermittent peripheral neuropathy. FIG. 4 provides data supporting the merit of utilizing the Patient Neurotoxicity Questionnaire (PNQ©), also known as the Peripheral Neuropathy Questionnaire, and the Generalized Estimating Equation (GEE) statistical method to evaluate intermittent and cumulative peripheral neuropathy. The results in FIG. 5 demonstrate that there was an approximate 50% reduction in severe (Grade D or E) intermittent or cumulative peripheral neuropathy in the patient population with non-small cell lung carcinoma (NSCLC) who were treated with a paclitaxel/Tavocept™/cisplatin regimen in comparison to those NSCLC patients who received a paclitaxel/saline placebo/cisplatin regimen.

Prior to the present invention, it was assumed within the medical community that the initial development of peripheral neuropathy would involve the continuation of the neurotoxic symptomology for, typically, approximately 7 months after the cessation of chemotherapy. In addition, electrophysiological abnormalities would last for years, and perhaps indefinitely, especially when there is evidence of platinum retention in the circulation even years after the treatment has been completed. See, e.g., Giatema, J., et al., Circulating plasma platinum more than 10 years after cisplatin treatment for testicular cancer. *Lancet* 355:1075 (2000). However, with the identification of this novel intermittent form of neuropathy, peripheral neuropathy can no longer be assumed to be a pathophysiology which occurs on a continuum.

The results set forth in the instant application represent an extremely important development for patients because this new knowledge will allow physicians to make better treatment decisions regarding patients with intermittent peripheral neuropathy who might otherwise have been improperly diagnosed and/or inadequately treated. Due to the fact that it is a reliable and highly sensitive diagnostic tool, the utilization of the Peripheral Neuropathy Questionnaire (PNQ©) as part of the process in identifying and treating intermittent peripheral neuropathy is of great clinical significance.

All patents, publications, scientific articles, web sites, and the like, as well as other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent also includes all of the claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A method for mitigating or alleviating intermittent and cumulative neuropathy in a subject, wherein said method is comprised of a Formula (I) Compound which is administered to the subject in a medically sufficient dosage; and wherein said Formula (I) compound has the structural formula:

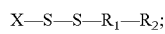

wherein;

$R_1$ is a lower alkylene, wherein $R_1$ is optionally substituted by a member of the group consisting of: lower alkyl, aryl, hydroxy, alkoxy, aryloxy, mercapto, arylthio, for a corresponding hydrogen atom, or

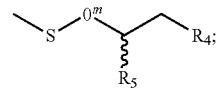

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide consisting of from 2-10 amino acids; or wherein X is a member of the group consisting of: lower thioalkyl (lower mercapto alkyl), lower alkylsulfonate, lower alkylphosphonate, lower alkylsulfonate, lower alkyl, lower alkenyl, lower alkynyl, aryl, alkoxy, aryloxy, mercapto, alkylthio or hydroxy for a corresponding hydrogen atom; and
pharmaceutically acceptable salts, conjugates, hydrates, solvates and polymorphs thereof.

2. A method for mitigating or alleviating intermittent neuropathy in a subject, wherein said method is comprised of a Formula (I) compound which is administered to the subject in a medically sufficient dosage; and wherein said Formula (I) compound has the structural formula:

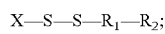

wherein;

$R_1$ is a lower alkylene, wherein $R_1$ is optionally substituted by a member of the group consisting of: lower alkyl, aryl, hydroxy, alkoxy, aryloxy, mercapto, arylthio, for a corresponding hydrogen atom, or

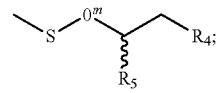

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide consisting of from 2-10 amino acids; or wherein X is a member of the group consisting of: lower thioalkyl (lower mercapto alkyl), lower alkylsulfonate, lower alkylphosphonate, lower alkylsulfonate, lower alkyl, lower alkenyl, lower alkynyl, aryl, alkoxy, aryloxy, mercapto, alkylthio or hydroxy for a corresponding hydrogen atom; and pharmaceutically acceptable salts, conjugates, hydrates, solvates and polymorphs thereof.

3. The method of claim 1 or claim 2, wherein said cumulative and/or intermittent neuropathy is caused by the diseases and/or treatments selected from the group consisting of: chemotherapy treatment, radiation treatment, and diabetes.

4. The method of claim 3, wherein said chemotherapy treatments comprise the administration of one or more chemotherapy agents selected from the group consisting of: platinum complexes and taxanes.

5. The method of claim 3, wherein said platinum complex medicaments are selected from the group consisting of: cisplatin, oxaliplatin, carboplatin, satraplatin, and derivatives and analogs thereof.

6. The method of claim 3, wherein said taxane medicaments are selected from the group consisting of: docetaxel, paclitaxel, polyglutamylated forms of paclitaxel, liposomal paclitaxel, and derivatives and analogs thereof.

7. The method of claim 3, wherein said administered platinum complex and taxane medicaments are cisplatin and paclitaxel.

8. The method of claim 1 or 2, wherein the diagnosis and treatment of said intermittent form of neuropathy is performed by administering a questionnaire to the subject, by the treating physician, or concurrently using both approaches.

9. The method of claim 8, wherein said questionnaire administered to the subject is the Peripheral Neuropathy Questionnaire (PNQ).

10. The method of claim 1 or 2, wherein said Formula (I) compound is a disodium salt.

11. The method of claim 1 or 2, wherein said Formula (I) compound is selected from the group consisting of: a monosodium salt, a sodium potassium salt, a dipotassium salt, a monopotassium salt, a calcium salt, a magnesium salt, an ammonium salt, or a manganese salt.

12. The method of claim 1 or 2, wherein said Formula (I) compound is disodium 2,2'-dithio-bis-ethane sulfonate.

13. The method of claim 1 or claim 2, wherein the dose of a Formula (I) compound ranged from approximately 14 g/m$^2$ to approximately 22 g/m$^2$.

14. The method of claim 13, wherein the dose of a Formula (I) compound is approximately 18.4 g/m$^2$.

* * * * *